(12) United States Patent
Baust et al.

(10) Patent No.: US 11,849,989 B2
(45) Date of Patent: *Dec. 26, 2023

(54) CRYOGENIC SYSTEM AND METHODS

(71) Applicant: Varian Medical Systems, Inc., Palo Alto, CA (US)

(72) Inventors: John G. Baust, Candor, NY (US); John M. Baust, Owego, NY (US); Anthony T. Robilotto, Binghamton, NY (US)

(73) Assignee: Varian Medical Systems, Inc., Palo Alto, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/316,073

(22) Filed: May 10, 2021

(65) Prior Publication Data

US 2021/0322082 A1    Oct. 21, 2021

Related U.S. Application Data

(63) Continuation of application No. 14/213,441, filed on Mar. 14, 2014, now Pat. No. 11,026,737.

(60) Provisional application No. 61/956,168, filed on Mar. 15, 2013.

(51) Int. Cl.
*A61B 18/02* (2006.01)
*A61B 18/00* (2006.01)

(52) U.S. Cl.
CPC .... *A61B 18/02* (2013.01); *A61B 2018/00023* (2013.01); *A61B 2018/00577* (2013.01); *A61B 2018/0212* (2013.01); *A61B 2018/0262* (2013.01); *A61B 2018/0293* (2013.01)

(58) Field of Classification Search
CPC .......... A61B 18/02; A61B 2018/00023; A61B 2018/00577; A61B 2018/0212; A61B 2018/0262; A61B 2018/0293
See application file for complete search history.

(56) References Cited

U.S. PATENT DOCUMENTS

| | | | |
|---|---|---|---|
| 3,794,039 | A | 2/1974 | Kollner et al. |
| 5,916,212 | A | 6/1999 | Baust et al. |
| 7,192,426 | B2 | 3/2007 | Baust et al. |
| 7,374,063 | B2 | 5/2008 | Reid et al. |
| 7,474,099 | B2 | 1/2009 | Boesel et al. |
| 7,681,299 | B2 | 3/2010 | Reid et al. |
| 2003/0055416 | A1 | 3/2003 | Damasco et al. |
| 2004/0215295 | A1 | 10/2004 | Littrup et al. |
| 2005/0261671 | A1 | 11/2005 | Baust |
| 2005/0261753 | A1 | 11/2005 | Littrup et al. |
| 2009/0012510 | A1 | 1/2009 | Bertolero et al. |
| 2011/0152849 | A1 | 6/2011 | Baust et al. |
| 2012/0059364 | A1 | 3/2012 | Baust et al. |

(Continued)

FOREIGN PATENT DOCUMENTS

| | | |
|---|---|---|
| EP | 2311398 | 4/2011 |
| WO | 2000/054684 | 9/2000 |

OTHER PUBLICATIONS

European Supplementary Search Report, dated Oct. 26, 2016, in EP Application No. 14764215.1.

*Primary Examiner* — Khadijeh A Vahdat
(74) *Attorney, Agent, or Firm* — Duane Morris LLP

(57) ABSTRACT

Embodiments of the present invention relate to cryogenic systems and methods useful to cool objects, including living tissue, to freezing or cryogenic temperatures by placing the object in thermal communication with sub-cooled supercritical nitrogen.

19 Claims, 6 Drawing Sheets

(56) References Cited

U.S. PATENT DOCUMENTS

2012/0253336 A1 10/2012 Littrup
2012/0271292 A1 10/2012 Duong et al.

CRYOGENIC SYSTEM AND METHODS

CROSS-REFERENCE TO RELATED APPLICATIONS

This application is a Continuation Application of U.S. patent application Ser. No. 14/213,441 filed Mar. 14, 2014, now U.S. Pat. No. 11,026,737, which claims benefit to U.S. Provisional Application No. 61/956,168 filed Mar. 15, 2013 which is herein incorporated by reference in its entirety.

FIELD OF THE INVENTION

Embodiments of the present invention relate to cryogenic systems and methods useful to cool objects, including living tissue, to freezing or cryogenic temperatures by placing the object in thermal communication with sub-cooled supercritical nitrogen.

BACKGROUND OF THE INVENTION

This application claims priority to U.S. Provisional Application No. 61/956,168 which is incorporated herein by reference.

There are numerous applications that involve cooling objects to freezing and below freezing temperatures. Examples of such applications are medical procedures referred to as cryoablation, cryotherapy or cryosurgery in which tissues and cells are cooled to sub-freezing temperatures to affect their death and eliminate them from the body. These medical procedures are commonly used (i) to kill unwanted tissue and cells such as, for example, for complete and partial elimination of tissues, glands and organs that contains cancerous or other unwanted or deleterious cells, and (ii) for cauterization of tissue and cells such as, for example, cauterization of cardiac tissue and cells that cause abnormal heart function.

Cryogenic methods involve lowering the temperature of objects, such as human and animal cells and tissue, by placing them in thermal communication with a cold temperature source that is capable of drawing heat out of or away from the object sufficient to lower the temperature of the object (including any surrounding material, if desired) to temperatures below freezing. In the case of medical applications, this cooling process kills the tissue or cells effectively eliminating these cells and tissue as well as, if desired, adjoining cells and tissue.

The cooling process involves removal of a heat load by a number of heat transfer mechanisms. One such mechanism is conduction, which involves heat transfer from a warmer object to a colder object by placing the objects in thermal communication with each other.

Current cryotherapy systems have certain drawbacks. For example, non-nitrogen-based systems use cryogens that (1) are more expensive to purchase, (2) are less available both inside and outside the U.S., and/or (3) are more tightly regulated, making them more administratively burdensome and expensive to use as a cryogen. Unlike non-nitrogen based systems, nitrogen is more readily available, is cheaper and is safer that most cryogens.

Some current nitrogen-based systems use nitrogen in different states (liquid and gaseous), each of which have characteristics that make them suboptimal for certain applications. For example, low pressure liquid nitrogen cannot flow and pass through structures with small inner diameter such as cryoprobe and cryocatheter supply lumens. Unlike nitrogen gas, the initiation of flow of liquid nitrogen through a small diameter lumen is inhibited or otherwise obstructed due to intermolecular forces that result in high surface tension and therefore, friction. Some nitrogen-based systems suffer from the phenomenon known in the art as "vapor lock," which can occur when liquid nitrogen flowing in a small diameter tube, such as is commonly required in a cryoprobe, transitions to the vapor phase as nitrogen gas thereby filling the cryoprobe tube or lumen causing the liquid nitrogen flow to stop as a result of (1) the large back pressure that results and (2) the relatively massive volume of expanding gas that forms in the tube or lumen. Attempts have been made to reduce the likelihood of vapor lock in nitrogen-based systems using nitrogen near its critical pressure and temperature.

Moreover, in methods and procedures involving the use of multiple cryoprobes, cryogenic systems must be able to reliably and consistently deliver a cryogen to multiple cryoprobes at a sufficient rate to simultaneously produce multiple ice balls and the ice balls must be of sufficient size to effectively kill the volumes of tissues required for effective therapy. Further, systems must be capable of reliably operating repeatedly so that multiple procedures can be performed with minimal interruption or delay.

Accordingly, there remains a need for nitrogen-based cryogenic systems and methods in which nitrogen can reliably and continuously flow small diameter lumens without being impeded by intra-fluid forces and without transitioning to a gas and causing vapor lock.

SUMMARY OF THE INVENTION

Cryogenic systems for cooling an exterior surface of a cryoprobe shaft using nitrogen as a cryogen are provided. In some embodiments, the comprises one or more cryoprobes, a dewar, at least one cryoengine, a supply line for connecting the cryoprobe to the cryoengine. The dewar includes a liquid nitrogen bath. Prior to use, a portion of the cryoengine is submerged in the liquid nitrogen bath. Supercritical nitrogen is generated by filling the cryoengine with a mixture of liquid nitrogen and nitrogen gas, sealing the cryoengine, adding heat continuously so the pressure increases and the nitrogen is exposed to high temperatures. Liquid nitrogen and nitrogen gas are provided at a ratio of from 0.75:1 to 1:0.75. Supercritical nitrogen forms in the cryoengine and is sub-cooled by the submersion of the cryoengine in liquid nitrogen. Embodiments of the system are adapted to provide negative pressure throughout the flow path. Upon initiating flow, sub-cooled supercritical nitrogen flows to the cryoprobes that are in contact with tissue. The tissue freezes as cryogen flows to the cryoprobe.

Apparatus and methods for generating sub-cooled supercritical nitrogen are provided.

Methods of using the sub-cooled supercritical nitrogen to cool cryoprobes for use in cryosurgical procedures are provided.

DETAILED DESCRIPTION

Overview

Figure 1:
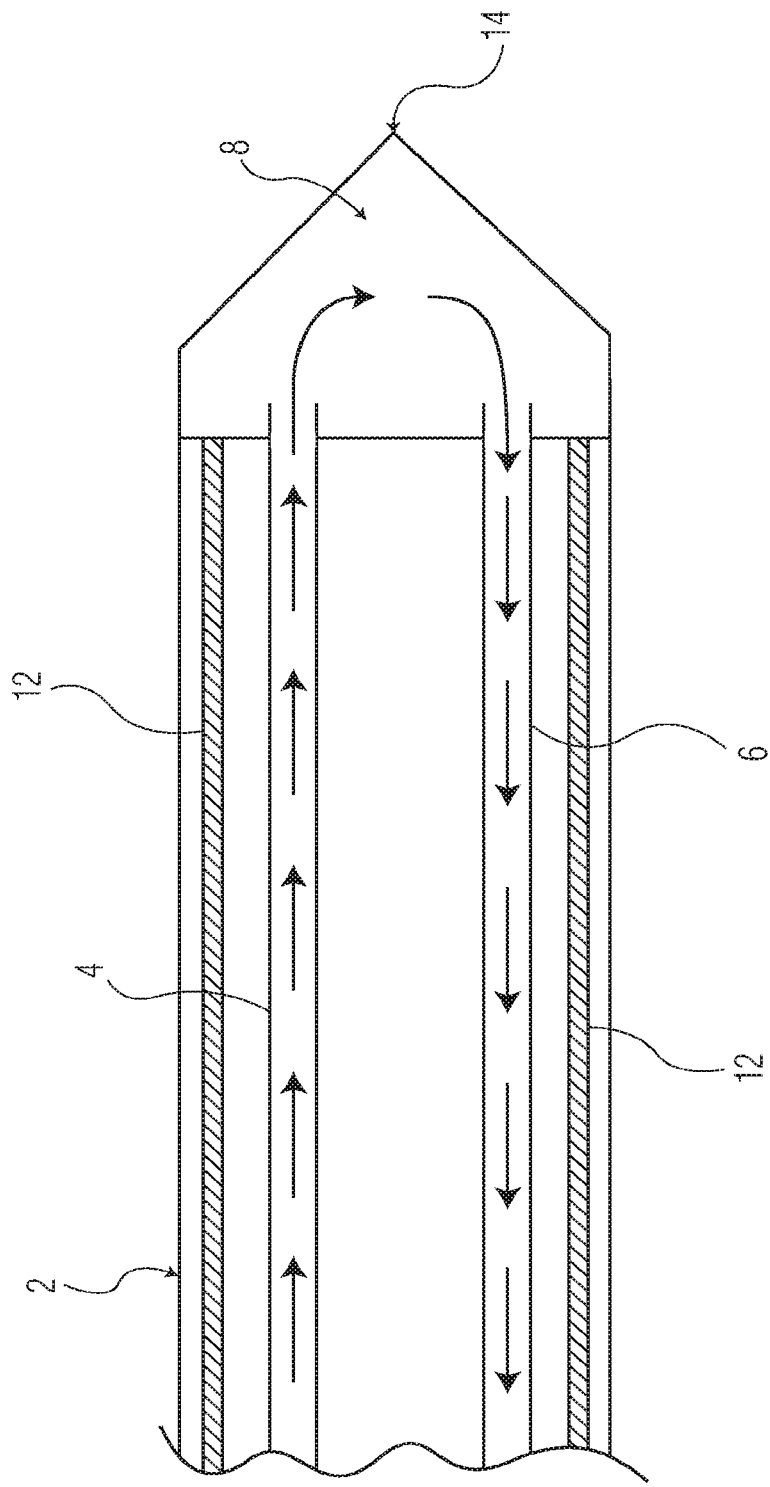
FIG. 1 depicts an embodiment of a cryoprobe.

Provided herein are cryoablation/cryosurgical/cryotherapy methods and other methods that include cooling an exterior surface of a cryoprobe, as well as cryogenic systems and devices useful in performing such methods. Methods for generating sub-cooled supercritical nitrogen are provided. In embodiments of the present invention, sub-cooled, supercritical nitrogen is circulated through a cryoprobe to cool an external surface of the cryoprobe and freeze cells and tissue brought into contact with the external surface of the cryoprobe.

In the methods and systems disclosed herein, sub-cooled, supercritical nitrogen is generated and used to initiate sub-cooled supercritical nitrogen flow through a small diameter supply lumen of a cryoprobe. Using a combination of liquid nitrogen and nitrogen gas in a cryoengine in a ratio of about 0.75:1.00 to 1.00:0.75, supercritical nitrogen is generated, pressurized to a pressure of 1000 psi or greater, and sub-cooled to a temperature of about −160° C. to about −170° C. The sub-cooled, supercritical nitrogen can then be used to initiate flow of sub-cooled, pressurized nitrogen to and through one or more cryoprobes where lethal ice formation on the exterior surfaces of the freeze zones of the one or more cryoprobes can be rapidly induced. Once flow of the sub-cooled, supercritical nitrogen through the cryoprobes occurs, the pressure of the sub-cooled, supercritical nitrogen can be steadily decreased from the initial pressure of 1000 psi or greater to a pressure of about 300 psi or less as the cryoengine is emptied of the sub-cooled, pressurized nitrogen contained therein. Simultaneously with the nitrogen flow, heat is absorbed by the sub-cooled, supercritical nitrogen and lethal ice formation occurs at the exterior surfaces of the freeze zones of the one or more cryoprobes.

In the methods and systems disclosed herein, supercritical nitrogen is sub-cooled prior to circulation through the one or more cryoprobes. That is, unlike other systems that rely on generating cold temperatures by isenthalpic expansion cooling, i.e., as a result of a pressure drop due to volume expansion of a pressurized gas (the Joule-Thomson effect), or by endothermic phase transition such as by evaporation that produces cold temperatures, methods and systems disclosed herein rely upon direct injection of sub-cooled nitrogen into the cryoprobe at a low or cryogenic temperatures. That is, with the current system, the nitrogen is delivered to the cryoprobe at cryogenic temperatures and not in a form in which the temperature drop occurs in the cryoprobe tip.

Cryoprobes used in the systems and methods described herein comprise a cryoprobe shaft, a cryoprobe supply lumen and a cryoprobe return lumen. The cryoprobe supply lumen and the cryoprobe return lumen extend within the cryoprobe shaft. The cryoprobe also includes a freeze zone within the cryoprobe shaft where the cryoprobe supply lumen is in fluid communication with the cryoprobe return lumen. The cryoprobe at the location of the freeze zone is thermally conductive. The interior surface of the cryoprobe at the freeze zone is in thermal communication with an external surface of the cryoprobe shaft at the freeze zone. At the freeze zone, the sub-cooled, supercritical nitrogen comes into contact with the interior surface that is thermally conductive and in thermal communication with an external surface of the cryoprobe shaft. Heat is transferred from the external surface of the cryoprobe shaft, particularly that portion of it which is in closest proximity to the interior surface of the freeze zone, and the external surface is cooled, particularly that portion of it which is in closest proximity to the interior surface of the freeze zone. Heat is likewise conducted from objects, such as tissue and cells that are in contact with the cooled external surface of the cryoprobe. As sub-cooled, supercritical nitrogen continues to flow through the freeze zone, heat continues to be transferred from the objects in contact with the cooled external surface to sub-cooled, supercritical nitrogen in the freeze zone. The amount of heat transferred is sufficient to form lethal ice and freeze the objects (tissue) in contact with the external surface of the cryoprobe.

The ice that is formed has a generally ellipsoid or generally spherical shape, and is commonly referred to as an ice ball. With the systems and methods disclosed herein, ice ball formation is rapid and predictable. Rapid, predictable ice ball formation is necessary and therefore highly desirable in cryosurgical/cryoablation procedures and results in (1) more controlled, accurate and precise destruction of targeted tissues while preserving the viability of adjacent healthy tissue, and (2) shorter procedure times. Systems disclosed herein are designed to generate sub-cooled, supercritical nitrogen at sufficient pressures to deliver the sub-cooled nitrogen to 1, 2, 3, 4, 5, 6, 7, 8, or more cryoprobes that are each connected to the system by a hose or umbilicus that is typically 12 or more feet in length and produces lethal ice at the external surface of the cryoprobe shaft adjacent to the freeze zone within 5-60 seconds of commencement of nitrogen flow when the cryoprobe is in living tissue, and in some embodiment within 5-25 seconds of commencement of nitrogen flow when the cryoprobe is in living tissue. In some embodiments using 1, 2, 3, 4, 5, 6, 7, 8, or more cryoprobes, ice is simultaneously produced on an external surface of the cryoprobe shaft of each cryoprobe in one minute or less, or in 45 seconds or less, or in 40 seconds or less, or in 35 seconds or less, or in 30 seconds or less, or in 25 seconds or less, or in 20 seconds or less, or in 15 seconds or less, or in 10 seconds or less, or in 5 seconds or less, from the commencement of nitrogen flow when the cryoprobe is in living tissue, in systems. Moreover, systems disclosed herein are able to reliably and consistently deliver sub-cooled supercritical nitrogen to multiple cryoprobes at a sufficient rate to simultaneously produce multiple ice balls of sufficient size to effectively eliminate or kill volumes of tissues required for effective therapy. Therefore, the present systems are more reliable and can be repeatedly so that multiple freeze/thaw cycles can be performed during a single procedure with minimal interruption or delay.

While various arrangements may be provided, the cryogenic systems disclosed herein generally comprise one or more cryoprobes, a dewar, one or more cryoengines, and a cryogen supply line that connects the one or more cryoprobes to the one or more cryoengines. The system also comprises ports and valves that allow for filling of the cryoengines with nitrogen by allowing the cryoengines to be isolated from the remainder of the system so the cryoengines can be filled with nitrogen and then pressurized in order to generate sub-cooled, supercritical nitrogen for delivery to the cryoprobes. In some embodiments, the system further comprises one or more system return lines. The dewar provides a liquid nitrogen bath in which at least one cryogen supply container is at least partially disposed. The liquid nitrogen bath supplies liquid nitrogen to at least one cryoengine and additionally sub-cools supercritical nitrogen in the at least one cryoengine through the partial submersion of the cryoengine in the liquid nitrogen bath in the dewar. The system comprises at least one cryoengine that heats, pressurizes, and sub-cools the cryogen within it. In order to pressurize the nitrogen in the system, the cryoengine that is disposed within the liquid nitrogen bath may include at least one internal heating element that heats the nitrogen in the cryoengine in order to raise the pressure of the system and generates supercritical nitrogen. The submersion of the cryoengine in liquid nitrogen bath sub-cools the supercritical nitrogen. In some embodiments, instead of, or in combination with the at least one heating element, the nitrogen system may be pressurized with at least one pump that is submersed in the cryoengine disposed within the liquid nitrogen bath, wherein the pump may be similar to that disclosed in commonly assigned U.S. Pat. No. 7,192,426, the entire contents of which are incorporated herein by reference in its entirety for all purposes (for example, the pump (1) may be a pump assembly that includes a driving mechanism coupled to an elongated drive shaft, a piston coupled to said drive shaft and adapted to be submersed in the nitrogen, a one-way inlet valve in fluid communication with the piston, a one-way outlet valve in fluid communication with the piston, and a supply manifold in fluid communication with the outlet valve, where the supply manifold includes at least one port for connection to a cryoprobe, and (2) may include a bellows). In some embodiments, a cryoengine is part of a cryogen distribution assembly, which may also be submerged in the liquid nitrogen bath. The submerged components of the cryogen distribution assembly function to further sub-cool the nitrogen flowing through it, thereby performing a function similar to a heat exchanger. The cryogen distribution assembly is used to supply sub-cooled, supercritical pressurized nitrogen from the cryoengine to the one or more cryoprobes. In some embodiments, the system further comprises sensors and monitoring devices such as temperature sensors, pressure sensors, and cryogen level sensors. In some embodiments, the system further comprises an operator interface that includes a display (which may be touch-screen) and/or a keypad and/or other input components to direct and monitor the operation of system. In some embodiments, the operator interface device is a computer including a display and keyboard. In some embodiments, the system further comprises imaging capabilities such as ultrasound and/or 3D imaging. Further, in some embodiments, the system may include (1) planning and guidance systems and software that help a doctor plan a cryotherapy procedure as well as guide the doctor during the procedure, and/or (2) an electronic medical records interface to allow the system to communicate with at least one electronic medical records database. Reference herein to "systems" includes an apparatus with cryoprobes or without cryoprobes as well as an apparatus having one, some or all of the above described components. In some embodiments, the system is portable and includes a base with locking wheels.

In some embodiments, heat, provided by the at least one heating element internal to the cryoengine within the liquid nitrogen bath, is used to pressurize the nitrogen above its critical pressure. Heat also serves to raise the temperature of nitrogen above its critical temperature. As a result, supercritical nitrogen is generated and sub-cooled through its contact with thermally conductive components of the system within the liquid nitrogen bath in the dewar in which the cryoengine is at least partially disposed. The sub-cooled, supercritical nitrogen generated by the system has characteristics that make it extremely effective for use as a cryogen in the present system. As disclosed in co-pending, commonly assigned U.S. patent application Ser. No. 13/038,862 (Publication No. 2012/0059364), the entire contents of which are incorporated herein by reference in its entirety for all purposes, Supercritical nitrogen is a dense fluid that has the properties of both a liquid and a gas. As a result, supercritical nitrogen lacks surface tension making it capable of frictionless flow. Accordingly, the sub-cooled, supercritical nitrogen can flow through the small inner diameter supply and return lumens of the cryoprobes unlike other nitrogen-based systems that do not operate in the high pressure, supercritical range. The system provides continuous flow of sub-cooled, supercritical nitrogen that is sufficient to rapidly freeze tissue through the formation of lethal ice. The ice balls generated by the present system can be produced rapidly, predictably, and simultaneously utilizing multiple cryoprobes in cryotherapy procedures having multiple freeze/thaw cycles.

Cryoprobes

Typically, cryoprobes are disposable, single use components that are detachably connected to the apparatus that generates the cryogen (the cryoengine). The embodiments of the present cryoengine generate and supply the sub-cooled supercritical nitrogen to one or more cryoprobes.

As depicted in FIG. 1, an embodiment of a cryoprobe for use with the present system comprises a cryoprobe shaft 2, a cryoprobe supply lumen 4, a cryoprobe return lumen 6, and a freeze zone 8. In addition, the cryoprobe may include an insulation element 12 to insulate the cryoprobe shaft to prevent frosting or icing on the cryoprobe shaft 2 outside of the freeze zone 8. In some embodiments, the insulation element may be a vacuum insulation sleeve similar to that disclosed in U.S. Pat. Nos. 7,374,063 and 7,681,299, the entire contents of both patents are incorporated herein by reference in their entirety for all purposes. Specifically, the vacuum insulation sleeve can include an interior and an exterior wall with an insulating space defined there between.

In some embodiments, the cryoprobe can be a variable cryoprobe similar to that disclosed in co-pending, commonly assigned U.S. patent application Ser. No. 13/539,749 (Publication No. 2012/0271292) (for example, the variable cryoprobe can include (a) a shaft for providing a heat exchange surface for cryogenic ablation, (b) a housing, (c) an insulation element slideably engaged with the shaft, and (d) an adjustable sliding apparatus including (i) a slider assembly attached to the insulation element for slideably guiding the insulation element within the shaft, and (ii) an actuation assembly operatively connected to the slider assembly for allowing a user to slide the slider assembly to provide a desired adjustment of the insulation element relative to the shaft, where the adjustable sliding apparatus comprises a button assembly, where the button assembly is operatively connected to the slider assembly for allowing a user to actuate the slider assembly to provide the desired adjustment of the insulation element, where the adjustable sliding apparatus permits a user to change a size of an ice ball created by the cryosurgical probe, and where the insulation element comprises a vacuum sleeve or tube). In addition, the cryoprobe may include a connector at its end opposite the freeze zone 8 that permits the cryoprobe to be connected to the cryoengine with flexible supply line or hose that is usually insulated.

Figure 2:
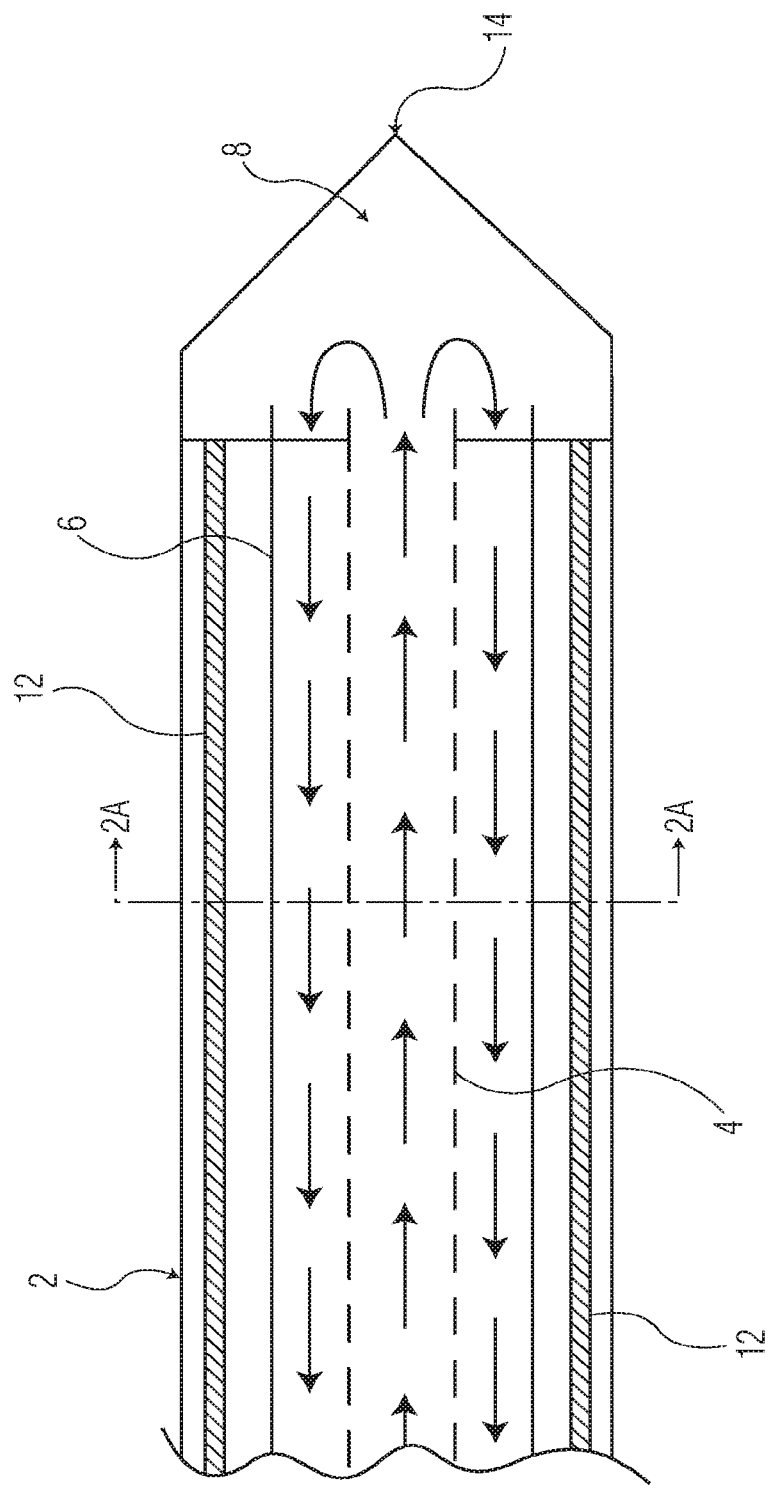
FIG. 2 depicts an embodiment of a cryoprobe.
Figure 2A:
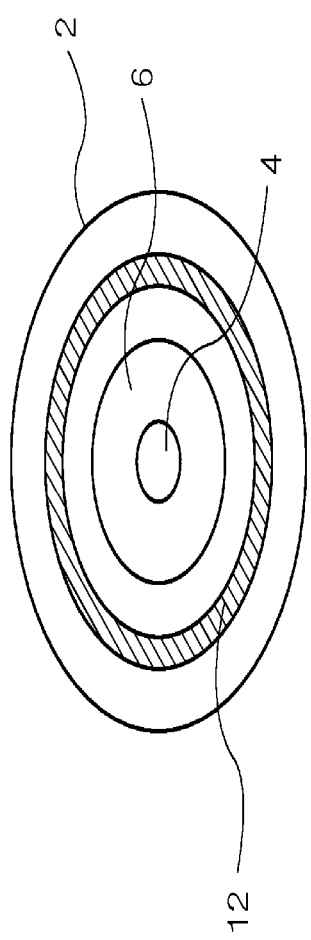
FIG. 2A depicts a cross-sectional view of the embodiment of a cryoprobe shown in FIG. 2.

As can be seen in FIG. 1, the cryoprobe supply lumen 4 and the cryoprobe return lumen 6 extend along the length of the cryoprobe shaft 2. In some embodiments, as depicted in FIG. 2, the cryoprobe supply lumen 4 has an outer diameter that is smaller than the inner diameter of the cryoprobe return lumen 6 such that the cryoprobe supply lumen 4 can extend through the cryoprobe return lumen 6. In such embodiments, it is common for the cryoprobe supply lumen 4 to extend within the cryoprobe shaft 2, slightly farther than the cryoprobe return lumen 6 into the freeze zone 8. Also in such embodiments, the outer diameter of the cryoprobe return lumen 6 is smaller than the inner diameter of the cryoprobe shaft 2 such that an insulation element 12 can be included between the exterior surface of the cryoprobe return lumen 6 and the interior surface of the cryoprobe shaft 2, where the insulation element 12 does not extend into the freeze zone 8. FIG. 2A depicts a cross-sectional view of the cryoprobe shown in FIG. 2. FIG. 2A shows that the cryoprobe supply lumen 4 has an outer diameter that is smaller than the inner diameter of the cryoprobe return lumen 6 such that the cryoprobe supply lumen 4 can extend through the cryoprobe return lumen 6. FIG. 2A also shows that the outer diameter of the cryoprobe return lumen 6 is smaller than the inner diameter of the cryoprobe shaft 2 such that an insulation element 12 can be included between the exterior surface of the cryoprobe return lumen 6 and the interior surface of the cryoprobe shaft 2. FIG. 2 shows the location of the cross-sectional view depicted in FIG. 2A. At that location, the cryoprobe contains insulation element 12 between the exterior surface of the cryoprobe return lumen 6 and the interior surface of the cryoprobe shaft 2 as shown in FIG. 2 and FIG. 2A. FIG. 2 shows that the insulation element 12 does not extend into the freeze zone 8.

As can be seen in FIGS. 1 and 2, the cryoprobe supply lumen 4 is in fluid communication with the cryoprobe return lumen 6 at the freeze zone 8. Furthermore, the cryoprobe shaft 2 is thermally conductive (typically, made from stainless steel) and the freeze zone 8 is in thermal communication with the cryoprobe shaft 2 thus allowing for conduction cooling of the shaft 2 at the freeze zone 8 as the sub-cooled, supercritical nitrogen flows or circulates through the freeze zone 8.

The cryoprobe shaft 2 is an elongated, wand-like structure that may be provided in various forms. In some embodiments, the cryoprobe shaft 2 is a thin flexible structure, such as in a cryocatheter, for example, or a vascular cryocatheter. Such configurations are particularly well-suited for inserting the cryoprobe into areas of the human body having defined channels, openings or passages which include turns and contortions such as blood vessels. In some embodiments, the cryoprobe shaft 2 is a thin, rigid, needle-like structure with a tissue piercing tip 14. Such configurations are particularly well-suited for percutaneous insertion directly into tissue including in cases in which piercing skin or tissue to access the tissue to be eliminated is not contra-indicated. Such a cryoprobe is typically used, for example, in prostate, liver, lung, kidney, breast, bone and bladder procedures.

The insulated flexible supply hose comprises a flexible supply lumen and a flexible return lumen. At the connection of the flexible hose to the cryoprobe, the flexible supply lumen is connected to and in fluid communication with the cryoprobe supply lumen 4. The flexible return lumen is connected to and in fluid communication with the cryoprobe return lumen 6. At the connection of the flexible hose to the cryoprobe assembly connector at the cryoengine, the flexible supply lumen is connected to an opening in the cryoprobe assembly connector, the counterpart of which is an opening in the system cryoprobe connector, which is connected to a system supply line such that the flexible supply lumen is in fluid communication with the system supply line, and in effect, the exit port of the cryoengine is in fluid communication with the cryoprobe supply lumen 4 and freeze zone 8. In those embodiments comprising a return line, the flexible return lumen is connected to an opening in the cryoprobe assembly connector, the counterpart of which is an opening in the system cryoprobe connector which is connected to a system return line such that the flexible return lumen is in fluid communication with the system return line, and in effect, the freeze zone 8 and cryoprobe return lumen 6 are in fluid communication with dewar.

Figure 3:
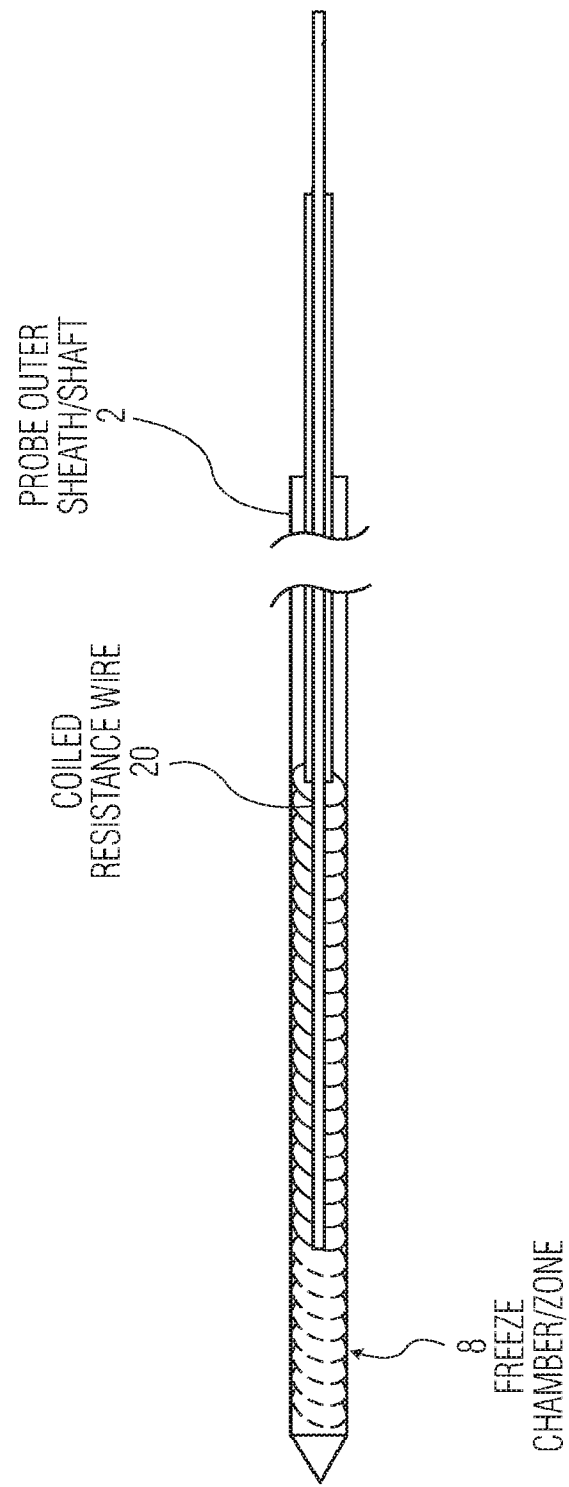
FIG. 3 depicts an embodiment of a cryoprobe with an electric thawing feature.

In order to heat the cryoprobe, for example, for a thawing cycle or to remove the cryoprobe from the patient, some embodiments of the cryoprobe may include thermoelectric warming (TEW) capabilities. In TEW, as depicted in FIG. 3, a resistance wire heater coil 20 is positioned within the internal lumen of the cryoprobe tip (i.e., the freeze zone 8), and following the freeze cycle, a low DC current is applied to the resistance wire heater coil 20 to effect warming of the metallic cryoprobe shaft 2 thereby thawing the ice ball formed around the tip of the cryoprobe. In some embodiments, the resistance wire heater coil 20 is a 35 Gauge 21 ohm Nicrome60 resistance wire with a heavy enamel insulation coating (35NiCr60-HML) connected in a coil configuration. Based on the diameter of the cryoprobe shaft 2, the outer diameter of the resistance wire heater coil 20 may be set to be ~0.065 in. to allow for the insulated resistance wire heater coil 20 to come into direct contact with the inner surface of the cryoprobe shaft 2 at the freeze zone 8 providing for direct thermal contact with the cryoprobe shaft 2 and ice ball generated. In some embodiments, the insulated resistance wire heater coil 20 operates at either 12V or 24V, where 12V provides 7.5 watts of power and 24V provides for 16.5 watts of power.

Dewar

Figure 4:
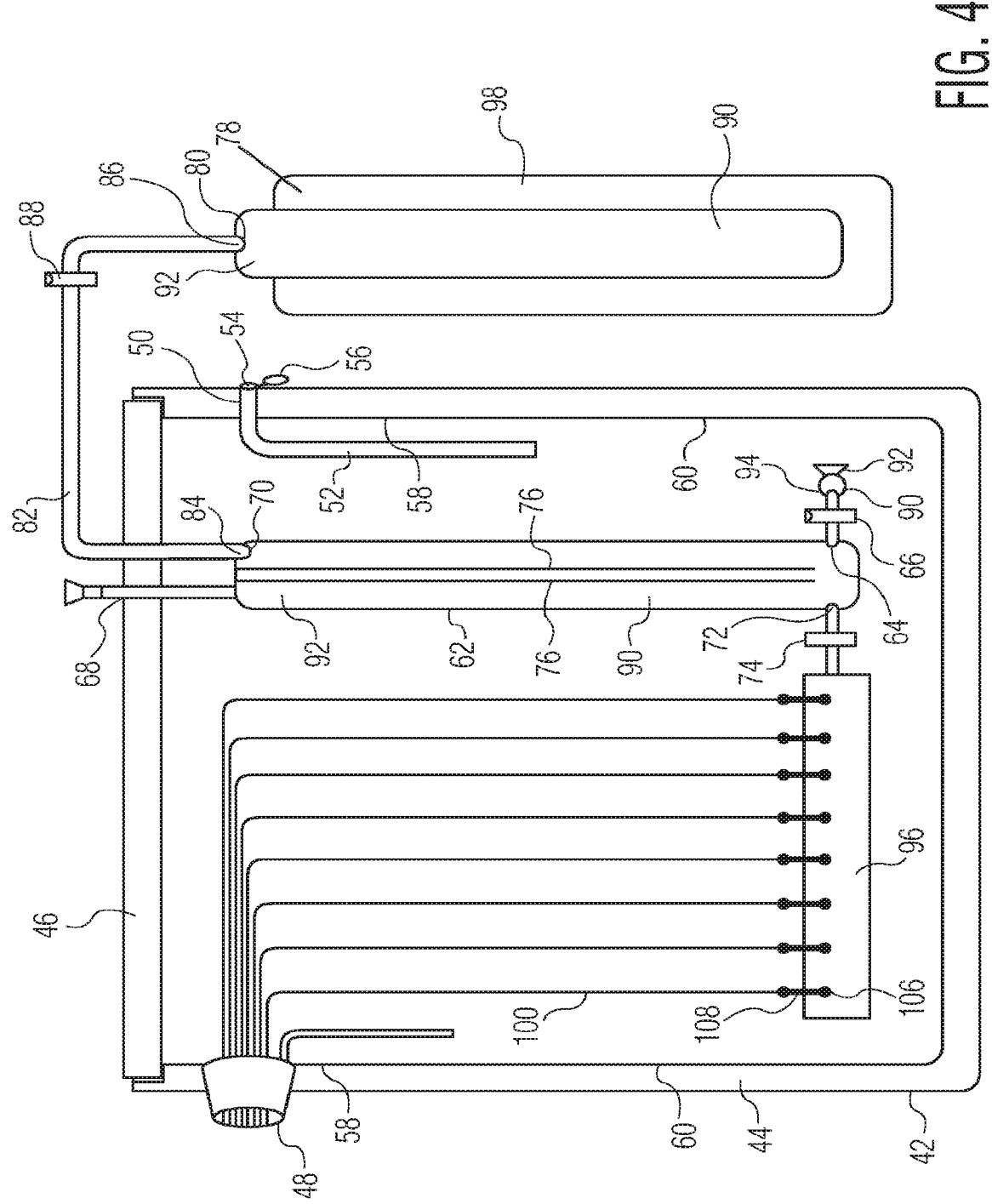
FIG. 4 depicts a single cryoengine system with a two tank cryoengine design.

In embodiments of the present invention, the dewar 42 is an insulated container 44 used to hold a liquid nitrogen bath. A portion of a cryoengine is submersed in the liquid nitrogen bath of the dewar. As shown in FIG. 4, the dewar 42 may comprise a lid or cover 46 and various openings 48 through which structures such as system supply lines and system return lines, power supply lines, components and structures of the cryoengine, etc., may pass. The dewar 42 may comprise an opening 50 through which liquid nitrogen can be added to the dewar 42 from an external source of liquid nitrogen such as a portable liquid nitrogen tank or a central liquid nitrogen supply tank. The opening 50 may be connected to a fill tube 52 which directs the flow of liquid nitrogen added into the insulated container 44. The opening 50 may have a connector or fitting 54 for receiving a connector attached to a hose or tubing of the external source and/or for receiving a cap or cover 56 when not being filled by an external source.

Typically, the dewar 42 includes a fill level 58 indicating a predetermined level that identifies the level in the dewar 42 representing a full liquid nitrogen bath. The dewar may also include a re-fill level 60 indicating a predetermined level that indicates the level in the dewar 42 representing a minimum amount of liquid nitrogen in the liquid nitrogen bath within recommended operating parameters. When the liquid nitrogen is at the re-fill level 60, liquid nitrogen is to be added to the dewar 42 so the liquid nitrogen bath is filled to operating levels. The dewar 42 may provide a visual access to the liquid nitrogen bath sufficient to allow an operator to determine if the liquid nitrogen bath is present in an amount to indicate it is at the fill level 58, between the fill level 58 and re-fill level 60, or at or below the re-fill level 60. In some embodiments, the dewar 42 is provided with a fill level sensor including the sensor system, such as a float sensor, electronic sensors, thermosensors and the like, used to measure fill levels, i.e. the amount of liquid nitrogen in the dewar 42, and a connection from the sensor to an indicator, a gauge, a computer with a display, and the like.

Cryoengine Generally

As used herein, the term "cryoengine" refers to the components of the systems described herein that can be used to produce nitrogen at a pressure of greater than 1000 psi and a temperature of less than −150° C.

The cryogenic systems provided herein may comprise one or more cryoengines. Systems comprising two or more cryoengines may be integrated so that they may use a common distribution assembly to supply cryogen to one or more cryoprobes. In such integrated systems, it may be possible to switch cryoengines being used to supply nitrogen to the distribution assembly during operation such that nitrogen can be provided continuously without interruption when one cryoengine is low or emptied of its nitrogen contents. In some embodiments, the system comprises a single cryoengine (see FIG. 4). In some embodiments, the system comprises two cryoengines arranged in parallel (see FIG. 5). In some embodiments, the system comprises three of more cryoengines arranged in parallel. In some embodiments comprising two or more cryoengines arranged in parallel, each cryoengine is connected to the distribution assembly by one or more valves that are configured so that each cryoengine can be selectively put in fluid communication with the distribution assembly while the remaining one or more cryoengines are closed off from the distribution assembly. Typically in such designs, one cryoengine may be used to deliver sub-cooled, supercritical nitrogen to the cryoprobes while sub-cooled, supercritical nitrogen in the one or more other cryoengines is being generated and prepared for use in such methods.

Each of the one or more cryoengines includes an inlet port, an opening though which it can be filled with nitrogen. Each cryoengine has an inlet valve connected to the inlet port so that when the valve is opened, the cryoengine can be filled and when closed, the cryoengine can be pressurized. Typically, the opening is a dedicated filling port connected to a valve.

Each cryoengine may comprise one or more containers or tanks. In some embodiments, a cryoengine has a single tank. In some embodiments, a cryoengine has two tanks (see FIG. 4 and FIG. 5). In some embodiments, a cryoengine has three, four, five or more tanks. In each instance where a cryoengine has two or more tanks, the tank interiors, also referred to as chambers, are in fluid communication. The tank of a cryoengine with a single tank has multiple openings, each of which can be closed with a cover or connected to a valve, which can be closed. When each opening is covered or connected to a closed valve, the interior of the tank is isolated and can be pressurized. In cryoengines with two tanks, the tanks are connected to each other by a conduit pipe and a valve. When the valve is closed, the chamber of one tank is isolated from the chamber of the other; when the valve is open, the chambers of the tanks are in fluid communication with each other. One or both of the two tanks includes additional openings. When each of these additional openings are closed with a cover or connected to a closed valve, and the valve connecting the two tanks is open, the combined tank chambers can be pressurized. Single cryoengines that have three or more tanks can be similarly arranged so that the interiors are in fluid communication with each other while all other openings are closed, thereby allowing for pressurization.

The cryoengine comprises at least one internal heat source and may comprise multiple internal heat sources. In addition, the cryoengine may comprise one or more external heat sources.

Two Tank Cryoengines

Figure 5:
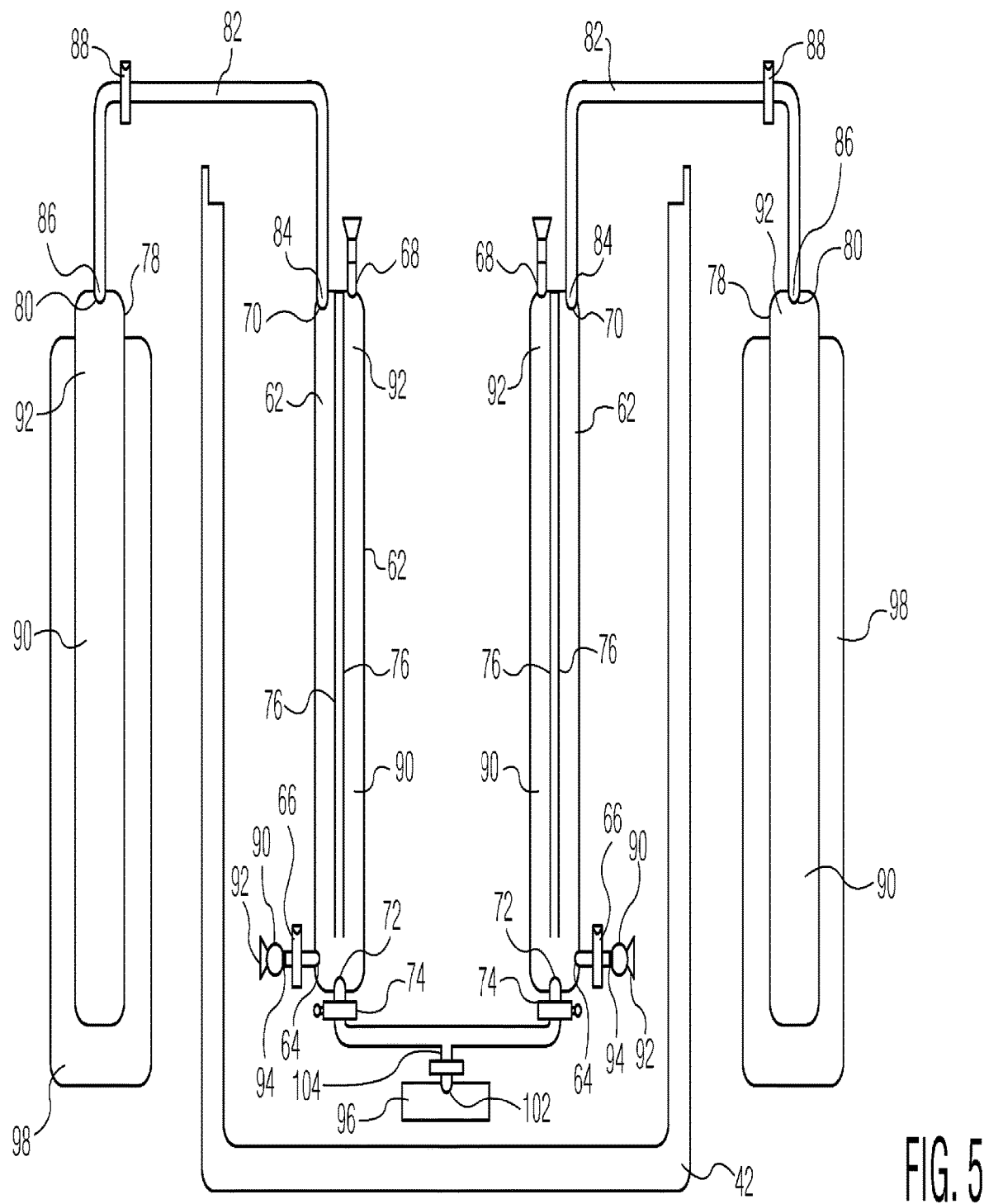
FIG. 5 depicts a two cryoengine system, each with a two tank cryoengine design.

While single tank cryoengines and cryoengines with three of more tanks are contemplated, the most common cryoengine design includes two tanks connected by a tank conduit tanks (FIG. 4 and FIG. 5). The two tanks are connected by the tank conduit such that the interior of each tank are in fluid communication with each other through the tank conduit.

Referring to FIG. 4 and FIG. 5, a first tank 62 may be provided that comprises a first tank inlet port 64 connected to a first tank inlet valve 66, a first tank vent valve 68, a first tank-conduit connector port 70, a first tank outlet port 72 connected to a first tank outlet valve 74, and one or more heating elements, such as an immersion heater 76 disposed within the first tank 62. A second tank 78 may be provided that comprises a second tank-conduit connector port 80. A tank conduit 82, which comprises at one end, a conduit-first tank conduit connector port 84 and at its other end, a conduit-second tank conduit connector port 86, may be provided to connect the first tank 62 to the second tank 78 and place the respective interiors of the first tank and the second tank in fluid communication. A tank conduit valve 88 may be optionally provided to allow for the control of fluid flow between the first tank 62 and the second tank 78 through the tank conduit 82. A submersible pump 90 may optionally be provided and connected to the first tank.

The first tank 62, also referred to as the charge tank or cryogen supply tank, is disposed at least partially in the dewar 42. When the dewar 42 contains a liquid nitrogen bath, the first tank 62 is at least partially submersed in the liquid nitrogen bath. In some embodiments, the portion of the first tank 62 submersed in the liquid nitrogen bath is made of a thermally conductive material so that heat can transfer from within the first tank 62 to the liquid nitrogen bath. In this way, the first tank 62 functions as a heat exchanger, lowering the temperature of its contents, or otherwise removing heat from the contents (nitrogen) of the first tank 62. Supercritical nitrogen generated in the cryoengine may be sub-cooled by the heat exchanger function of the partially or fully submersed first tank. In some embodiments, the first tank 62 is inside the dewar 42 such that when the dewar 42 contains the liquid nitrogen at or near a liquid nitrogen bath fill line 58, initially at least 75%, 80%, 85%, 90% or 95% or more of the first tank is submersed in the liquid nitrogen bath. In some embodiments, the first tank 62 is inside the dewar 42 such that when the dewar 42 contains the liquid nitrogen, the first tank 62 is fully submersed in the liquid nitrogen bath. The first tank may have a volume of 0.5 liters or less up to 5 liters or more. In some embodiments, the first tank may have a volume of 0.5 liters, 1 liter, 1.5 liters, 2 liters, 2.5 liters, 3 liters, 3.5 liters, 4 liters, 4.5 liters, or 5 liters or more. In some embodiments, the first tank is about 3.7 liters.

The first tank comprises a first tank inlet port 64, a first tank vent valve 68, a first tank-conduit connector port 70, and a first tank outlet port 72. While it is possible to arrange piping and valves so that two or more these openings can be provided in piping connected to a single opening rather than as separate openings in the first tank, embodiments include those in which each of the first tank inlet port 64, the first tank vent valve 68, the first tank-conduit connector port 70, and the first tank outlet port 72 are separate openings in the tank body of the first tank 62. Additional openings may be optionally provided such as a first tank access port that is sealed with a first tank access door, and openings to provide access for electrical and electronic connections, power supply connectors, sensor connectors, and the like. In some embodiments, the first tank access port is a removable closure that seals a first tank access port at the top of the first tank. In some embodiments, the removable closure at the top of the first tank contains electrical connections to connect to internal electrical components such as sensors and immersion heaters. In some embodiments, electrical connections are integrated into the first tank 62.

The first tank 62 comprises an internal heat source, which can be one or more heating elements such as one or more immersion heaters 76. In some embodiments, the cryoengine comprises one, two, three, four or more immersion heaters 76 in the first tank 62. Each of the one or more heating elements 76 may, independently be an immersion heater of 500 Watts or less up to an immersion heater 76 of 2000 Watt or more. In some embodiments, each immersion heater 76 may be a 500 Watt immersion heater, a 1000 Watt immersion heater, a 1500 Watt immersion heater or a 2000 Watt immersion heater. Typically, the heating elements are attached to the inside of the first tank at or near the top of the tank and extend longitudinally downward within the first tank 62. The heating elements may be attached at or near center of the top of the first tank so that they extend longitudinally within the first tank 62 along its center line such as along or near its longitudinal axis such that they are centrally located within the tank. An electrical connection, which is connected to a power supply, is provided from the exterior of the first tank and connected to the internal heating source(s) inside the first tank so that the internal heat source(s) can be connected to and energized by a power supply.

The first tank 62 may comprise one or more temperature sensors inside the first tank including connections to connect the one or more temperature sensors 90 within the first tank 62 to temperature monitoring equipment outside the first tank 62. Some embodiments comprise multiple temperature sensors 90 inside the first tank 62 arranged to be at different depths within the first tank 62 in order to measure the temperature at the various depths within the first tank 62 and allow for fill level to be determined. In some embodiments, one or more temperature sensors 90 within the first tank are attached at a location near the top within the first tank. In some embodiments, one or more temperature sensors 90 inside the first tank 62 are thermocouples and the first tank 62 contains connections to connect the one or more thermocouples within the first tank to a power source and temperature monitoring equipment outside the first tank.

The first tank 62 optionally contains one or more pressure sensors 92 inside the first tank, including connections to connect the one or more pressure sensors within the first tank to pressure monitoring equipment outside the first tank. In some embodiments, one or more pressure sensors 92 within the first tank are attached at location near the top within the first tank. In some embodiments, one or more pressure sensors are connected to one or more pressure gauges or to other pressure monitoring equipment linked to a computer outside the first tank.

The first tank optionally contains one or more temperature sensors inside the first tank, one or more temperature sensors, including connections to connect the one or more pressure sensors within the first tank to temperature monitoring equipment outside the first tank.

The first tank optionally contains one or more sensors, which monitor the amount of liquid nitrogen in the first tank, including connections to connect the one or more fill level sensors within the first tank to fill level monitoring equipment outside the first tank.

In some embodiments, a series of temperature sensors are provided at different longitudinal positions in the first tank. This series of temperature sensors provides, in addition to temperature information, information indicating the amount of liquid nitrogen in the first tank as it is being filled.

The first tank 62 may be filled with liquid nitrogen through the first tank inlet port 64. The first tank inlet port 64 is at the bottom or near the bottom of the first tank. The first tank inlet port 64 is connected to a first tank inlet valve 66, which is open when the first tank 62 is being filled and closed when the cryoengine is pressurized. In some embodiments, the first tank inlet valve 66 is a check valve. In some embodiments, the first tank inlet port 64 is connected to a first tank inlet valve 66, which is disposed in the dewar 42. When the dewar 42 contains a liquid nitrogen bath, the first tank inlet port 64 and the first tank inlet valve 66 is submersed in the liquid nitrogen bath.

In addition to being connected to the submersed first tank inlet port 64, the first tank inlet valve 66 may be connected to a submersible pump 90 disposed in the dewar 42. The submersible pump 90 comprises a pump inlet port 92 and a pump outlet port 94. The submersible pump 90 is connected to the first tank inlet valve 66 at the pump outlet port 94. When the dewar 42 contains a liquid nitrogen bath, the first tank inlet port 64, the first tank inlet valve 66 and the submersible pump 90 are submersed in the liquid nitrogen bath. The submersible pump 90 is connected to a power supply and when energized, the submersible pump is activated and pumps liquid nitrogen from the liquid nitrogen bath in the dewar 42 into the first tank 62. The liquid nitrogen enters the submersible pump 90 though the pump inlet port 92 and is pumped out through the pump outlet port 92, flows through the first tank inlet valve 66, through the first tank inlet port 64 and into the first tank 62. Providing the first tank inlet valve 66 as a check valve in this arrangement has the advantage of providing a one way valve that is only open when the cryogen is flowing from the submersible pump 90 into the first tank 62. The check valve will open by the positive pressure of the cryogen being pumped by the submersible pump 90 and will be closed by back pressure of the contents of the first tank 62. In some embodiments, the submersible pump is a brass, geared, rotary submersible pump. In some embodiments, the submersible pump pumps 4 liters/minute.

The first tank vent valve 68 is provided to allow gas to be purged from the first tank 62 when the first tank 62 is being filled with liquid nitrogen. In some embodiments, the first tank vent valve 68 may be located at or near the top of the first tank. In some embodiments, the first tank vent valve 68 may be an actuated valve such as an electric actuated check valve. During the filling process the first tank vent valve 68 is open and gas exits the first tank 62 as it becomes displaced by liquid nitrogen. When the first tank 62 is filled the first tank vent valve 68 is closed.

The first tank may have a direct external supply opening and valve that may be used to fill the first tank with liquid nitrogen supplied directly from an external supply tank to the first tank rather than using liquid nitrogen in the liquid nitrogen bath as the source of liquid nitrogen to fill the first tank.

The first tank-conduit connector port 70 is the opening in the first tank 62 to which the tank conduit 82 is connected in order to connect the first tank 62 to the second tank 78 and place the interior of the first tank in fluid communication with the second tank. In some embodiments, the first tank-conduit connector port 70 is at or near the top of the first tank such as in the upper half of the first tank, such as, for example, the upper quarter of the first tank, and in some embodiments at the upper tenth of the first tank. In some embodiments, the first tank-conduit connector port is at the center of the first tank. In some embodiments, the first tank-conduit connector port is at the bottom of the first tank or near the bottom of the first tank such as in the lower half of the first tank, such as, for example, the lower quarter of the first tank, and in some embodiments at the lower tenth of the first tank.

The first tank outlet port 72 is the opening in the first tank 62 to which the distribution assembly 96 is connected. The first tank outlet port 72 is connected to a first tank outlet valve 74 that is closed when the first tank 62 is being filled with liquid nitrogen, closed when the cryoengine is pressurized, and opened when nitrogen is being delivered to the cryoprobes. The first tank outlet port 72 is at the bottom of the first tank 62 such that liquid nitrogen from the first tank 62 is always drawn into the first tank outlet port 72 as the tank is emptied. In some embodiments, the first tank outlet port 72 may be at a location selected from a location at the bottom of the first tank, near the bottom of the first tank or at the lower tenth of the first tank.

The second tank 78 (also referred to as the pressure tank) is located outside liquid nitrogen bath and in most instances, outside of the dewar 42. Generally, the second tank 78 may have a volume of 0.5 liters or less up to 5 liters or more. In some embodiments, the second tank 78 may have a volume of 0.5 liters, 1 liter, 1.5 liters, 2 liters, 2.5 liters, 3 liters, 3.5 liters, 4 liters, 4.5 liters, or 5 liters or more. In some embodiments, the second tank 78 is about 3.7 liters. The second tank 78 comprises a second tank-conduit connector port 80, which is the opening in the second tank 78 to which the tank conduit 82 is connected in order to connect the second tank 78 to the first tank 62 and place the interior of the second tank in fluid communication with that of the first tank. Additional openings may be optionally provided such as a second tank access port that is sealed with a second tank access door, and openings to provide access for electrical and electronic connections, power supply connectors, sensor connectors, and the like. In some embodiments, the second tank access port is a removable closure that seals a second tank access port at the top of the second tank. In some embodiments, the removable closure at the top of the second tank contains electrical connections to connect to internal electrical components such as sensors. In some embodiments, electrical connections are integrated into the second tank. In some embodiments, the second tank comprises one or more temperature sensors in its interior. In some embodiments, the second tank comprises one or more pressure sensors.

Insulation 98 and/or one or more external heat sources may optionally be provided in direct contact with exterior surfaces of the second tank and/or tank conduit. In some embodiments, external heat sources may be placed in direct contact with portions of the non-submersed exterior surface of the first tank. Typically, any external heat source in contact with an exterior surface of the second tank and/or the tank conduit and/or non-submersed portion of the first tank, is thermally conductive and in thermal communication with the interior of the second tank and/or the tank conduit and/or non-submersed portion of the first tank. External heat sources may be insulated blankets or jacket heaters, drum blanket heaters, heating tape and the like. In some embodiments, exterior surfaces of the second tank and/or the tank conduit and/or non-submersed portion of the first tank are insulated or otherwise thermally non-conductive to prevent heat from radiating from the second tank and/or the tank conduit and/or non-submersed portion of the first tank.

The tank conduit 82 may be a pipe, tube or other structure or structures used to place the interior of first tank in fluid communication with the interior of the second tank.

The tank conduit 82 is connected to the first tank 62 by connection of the tank conduit's conduit-first tank conduit connector port 84 to the first tank's first tank-conduit connector port 70. The tank conduit 82 is connected to the second tank 78 by connection of the tank conduit's conduit-second tank conduit connector port 86 to the second tank's second tank-conduit connector port 80.

In some embodiments, the tank conduit 82 comprises one or more tank conduit valves 88. In some embodiments, a tank conduit valve 88 is provided that, when opened places the interior of first tank in fluid communication with the interior of the second tank through the tank conduit, and when closed isolates the interior of the first tank from the interior of the second tank and prevents fluid from passing between the interior of first tank and the interior of the second tank through the tank conduit. The tank conduit valve is located between the first tank and the second tank and may be located at the first tank-conduit connector port of the first tank, at the conduit-first tank connector port of the tank conduit, at a location anywhere along the length of the tank conduit, at the conduit-second tank connector port of the tank conduit, or at the second tank-conduit connector port of the second tank. The tank conduit valve may be integrated into or connected to the first tank-conduit connector port of the first tank. The tank conduit valve may be integrated into or connected to the pressure tank-conduit connector port of the pressure tank. A tank conduit valve may be integrated into or connected to either or both of the ends of the tank conduit. In some embodiments, the tank conduit valve is inserted into the tank conduit or connected on either side to piping, tubing or other components between the tank conduit valve and either the conduit-first tank connector port, or the conduit-second tank connector port or both. In the case of both, the tank conduit is made up of more than one segment, divided by the tank conduit valve, for example. If provided, the tank conduit valve may be closed during filling of the first tank with liquid nitrogen and opened when pressurization is commenced. The tank conduit valve may be closed prior to releasing pressure in the first tank in preparation for refilling the first tank with liquid nitrogen. In some embodiments, a tank conduit valve is a an actuated valve, such as an electric actuated valve. In some embodiments, the tank conduit valve is a pneumatic actuated valve or a hydraulic actuated valve. The tank conduit may have a total of volume of. 10 liters or less to a volume of 1.0 liters or more. In some embodiments, volume of the tank conduit is about 0.10 liters, about 0.15 liters, about 0.20 liters, about 0.25 liters, about 0.30 liters, about 0.35 liters, about 0.40 liters, about 0.45 liters, about 0.50 liters, about 0.55 liters, about 0.60 liters, about 0.65 liters, about 0.70 liters, about 0.80 liters, about 0.85 liters, about 0.90 liters, about 0.95 liters, or about 1.0 liters or more.

Each opening of a cryoengine is connected to a valve so that when each valve is closed, other than valves to the openings through which the tanks are connected, the cryoengine is a closed unit that can be pressurized.

In some embodiments, the ratio of the volume of the first tank to volume of the second tank may be a ratio of about from 0.75:1 to 1:0.75, about from 0.80:1 to 1:0.80, about from 0.80:1 to 1:0.80, about from 0.85:1 to 1:0.85, about from 0.90:1 to 1:0.95, about from 1.05:1 to 1:1.05, about from 1.10:1 to 1:1.10, about from 1.15:1 to 1:1.15, about from 1.20:1 to 1:1.20, about from 1.25:1 to 1:1.25, about from 1.30:1 to 1:1.30, or about from 1.35:1 to 1:1.35. In some embodiments, the ratio of the volume of the first tank to the volume of the second tank may be a ratio of about 1:1. In calculating the ratio, the volume of the second tank may or may not refer to the total volume of the second tank plus the volume of the tank conduit provided the volume of the tank conduit does not exceed about 15% of the total volume of the first tank and second tank combined. If the volume of the tank conduit exceeds 15% of the total volume of the first tank and second tank combined, the amount of tank conduit volume in excess of 15% of the total volume of the first tank and second tank combined is included in the volume of the second tank for purposes of calculated the ratio.

Cryogen Distribution Assembly

The cryogen distribution assembly comprises one or more cryogen supply lines. The cryogen distribution assembly functions to connect the cryoengine to the one or more cryoprobes. One or more valves are provided that when closed, prevent the flow of cryogen from the cryoengine to the cryoprobes. Typically, an exit port valve is provided at the exit port of the cryoengine. When this valve is closed, cryogen is prevented from flowing to the cryogen distribution assembly; when this valve is opened, cryogen can flow from the cryoengine to the cryogen distribution assembly. The exit valve may be integrated into or attached to the cryoengine or it may be used to connect the cryoengine to the cryogen distribution assembly or it may be integrated into a component of the cryogen distribution assembly such as into a distribution manifold or cryogen supply line.

In its simplest form, the cryogen distribution assembly is a supply line connecting a cryogen outlet port or cryogen exit port of the cryoengine to a cryoprobe. The system cryoprobe connector functions to receive one or more cryoprobe assembly connectors and thereby connect one or more cryoprobes to the apparatus in a manner so that cryogen can flow from the cryoengine to the cryoprobe supply lumen 4 and freeze zone 8. In some embodiments, the cryogen distribution assembly may connect the cryoengine to two or more system supply lines. When connected to two or more system supply lines 100, the cryogen distribution assembly may include a distribution manifold 96 with one or more inlets connected to one, two or more cryoengines and a plurality of outlet ports, each outlet port connected to a system supply line. In some embodiments, the distribution manifold contains a single inlet connected to one or more cryoengines. In embodiments in which the distribution manifold 96 contains a single inlet 102 connected to two or more cryoengines, the first tank outlet port 72 of each cryoengine feeds cryogen to the single distribution manifold inlet 102 through a common outlet conduit 104. In some embodiments, the cryogen distribution assembly may include a distribution manifold 96 with 1, 2, 3, 4, 5, 6, 7, 8, 9, 10, 11, 12 or more manifold outlet ports, each manifold outlet port 106 connected to a system supply line 108.

Typically, the cryogen distribution assembly comprises a distribution manifold, one or more cryoprobe supply lines and a system cryoprobe connector. The distribution manifold typically has a single inlet port that connects to one or more cryoengine outlet ports. The distribution manifold typically connects to multiple cryogen supply lines. In some embodiments, each of the multiple cryogen supply lines may connect to one of multiple system cryoprobe connectors. In some embodiments, multiple cryogen supply lines may connect to a single system cryoprobe connector which can receive multiple cryoprobe assembly connectors.

The cryogen distribution assembly is typically located at or near the bottom of the first tank. The cryogen distribution assembly may be located completely inside the dewar, partially inside the dewar or completely outside the dewar. If located inside the dewar, the cryogen distribution assembly may be fully submersed, partially submersed or not submersed when the dewar contains the liquid nitrogen bath above a minimum fill level.

In some embodiments, the distribution manifold is attached to the first tank at or near the bottom of the first tank. Further, some or portions of the cryogen supply lines connected to the distribution manifold are also submerged in the liquid nitrogen bath. Typically, the distribution manifold is fully submersed in the liquid nitrogen bath as are portions of the cryogen supply lines connected to the distribution manifold. The portions of the cryogen supply lines connected to the system cryoprobe connector and the system cryoprobe connector are typically not submerged in the liquid nitrogen bath. When the cryogen distribution assembly is fully submersed or partially submersed in the liquid nitrogen bath, such as embodiments which comprise a distribution manifold that is fully submersed in the liquid nitrogen bath together with portions of the cryogen supply lines are submersed in the liquid nitrogen bath and other portions of the cryogen distribution assembly such as the piping connecting the distribution manifold to the cryoengine, some of the submerged structures may be thermally conductive and therefore, function as a heat exchanger, lowering the temperature, or otherwise removing heat from the nitrogen that flows through the submersed structures further cooling the nitrogen.

In embodiments comprising a single cryoengine, the one or more valves connecting the cryoengine to the cryogen distribution assembly are configured so when closed, the cryoengine is not in fluid communication with the cryogen distribution assembly. In embodiments comprising two or more cryoengines, the one or more valves connecting the two or more cryoengines to the cryogen distribution assembly are configured so the valves can all be closed so that each cryoengine is not in fluid communication with the cryogen distribution assembly, or one or more valves can be opened so that only one cryoengine of the multiple cryoengines is in fluid communication with the cryogen distribution assembly.

In some embodiments, a cryogen distribution assembly that further comprises a distribution supply valve may be provided in which there may be a distribution supply valve between the first tank exit port and the distribution inlet port of the cryogen distribution assembly. In some embodiments, a cryogen distribution assembly that further comprises a distribution supply valve may be provided in which there may be a distribution supply valve between the distribution inlet port of the cryogen distribution assembly and the one or more cryoprobe supply. In some embodiments, the cryogen distribution assembly may comprise a distribution inlet port, a section of supply tubing and one or more cryoprobe supply ports, in some embodiments, 1-12 or more cryoprobe supply ports.

In some embodiments, the cryogen distribution assembly may comprise a distribution supply valve, a distribution inlet port, a section of supply tubing and one or more cryoprobe supply ports, the distribution supply valve being located between the first tank exit port and the distribution inlet port. In some embodiments, the cryogen distribution assembly may comprise a distribution supply valve, a distribution inlet port, two sections of supply tubing and one or more cryoprobe supply ports, the distribution supply valve being located between the individual sections of supply tubing. In some embodiments, the cryogen distribution assembly may comprise a distribution supply valve, a distribution inlet port, a section of supply tubing and one or more cryoprobe supply ports, the distribution supply valve being located between the supply tubing and the one or more cryoprobe supply ports. In some embodiments, the cryogen distribution assembly may comprise a distribution inlet port, one or more sections of supply tubing, a distribution manifold located outside of the dewar, and one or more cryoprobe supply ports connected to the distribution manifold. In some embodiments, the cryogen distribution assembly may further comprise a distribution supply valve located between the first tank exit port and the distribution inlet port, or between the distribution inlet port and a section of supply tubing, or between two sections of supply tubing, or between a section of supply tubing and the distribution manifold, or between the distribution manifold and the one or more cryoprobe supply ports. Each of the one or more cryoprobe supply ports may comprise a valve.

The cryogen distribution assembly may comprise one or more system supply lines (also referred to as cryogen supply lines) that are each attached to a system cryoprobe connector. Each of the one or more system supply lines may comprise a valve to allow, prevent or otherwise control the flow of cryogen through the supply lines of a cryoprobe attached to the system supply line that comprises the valve. In some embodiments, flow of cryogen from a system supply line to a supply line of a cryoprobe may be controlled by a valve on the cryoprobe such as, for example, at or near the cryoprobe handle where the cryoprobe is attached to a flexible hose.

The cryogen distribution assembly may comprise one or more system cryoprobe connectors. The system cryoprobe connector is linked to a system supply line from the distribution manifold. The system cryoprobe connector is typically also linked to a system return line, which extends from the connector to the dewar to deliver any cryogen flowing through the system return line into the liquid nitrogen bath. Such systems are commonly referred to as closed or semi-closed systems. In some embodiments, a system return line is not provided. Such embodiments require a venting component that facilitates cryogen flowing from the cryoprobe return lumen to reach temperature and pressure near ambient conditions before venting into the atmosphere. Such embodiments are commonly referred to as open systems.

System cryoprobe connectors and cryoprobe assembly connectors are configured to connect to each other and place supply lines in fluid communication. A system cryoprobe connector has an opening to which a system supply line is attached and a cryoprobe assembly connector has a corresponding opening, which is connected to the flexible supply lumen of the insulated hose or cryoprobe supply lumen. When a system cryoprobe connector is connected to a cryoprobe assembly connector, the system supply line connected to the system cryoprobe connector is in fluid communication with the supply lumen connected to the cryoprobe assembly connector. If return lines are in use, the system cryoprobe connectors and cryoprobe assembly connectors are configured to place return lines in fluid communication as well. A system cryoprobe connector has an opening to which a system return line is attached and a cryoprobe assembly connector has a corresponding opening, which is connected to the flexible return lumen of the insulated hose or cryoprobe return lumen. When a system cryoprobe connector is connected to a cryoprobe assembly connector, the system return line connected to the system cryoprobe connector is in fluid communication with the return lumen connected to the cryoprobe assembly connector.

In some embodiments comprising multiple system supply lines and multiple system cryoprobe connectors, each system cryoprobe connector is attached to a single system supply line. In some embodiments comprising multiple system supply lines, multiple system supply lines are connected to a single system cryoprobe connector. In some embodiments, a system cryoprobe connector is configured to receive a single cryoprobe assembly connector. In some embodiments, a system cryoprobe connector is configured to receive multiple cryoprobe assembly connectors. In some embodiments, a system cryoprobe connector is configured to receive a bundle or trunk line comprising multiple cryoprobe assembly connectors integrated in a single bundle or trunk line having multiple supply lumens. Single bundle or trunk lines are typically flexible and insulated and allow for a single line to be used from which individual cryoprobes can be supplied, thereby supplying multiple cryoprobes without having multiple supply hoses running from the device directly to the patient. A single trunk line brings multiple supply lines from the device to a central location close to the location of the patient and typically includes multiple return lines which carry cryogen away from the patient through a single multi-lumen trunk. Individual cryoprobes may be attached to a connector at the end of the trunkline near the location near the patient.

In some embodiments, the connectors link the flexible return lumen of the cryoprobe to a cryoprobe return line in the system that connects the system cryoprobe connector to the dewar. Such a configuration provides a closed or semi-closed system in which cryogen can flow from the cryo-engine, through the distribution assembly, and through the cryoprobe assembly. The cryogen delivered to the cryoprobe assembly flows through the flexible supply lumen within the insulated supply hose, through the supply lumen 4 of the cryoprobe, through the freeze zone 8, through the return lumen 8 of the cryoprobe, and through the flexible return lumen within the insulated supply hose, through the cryoprobe assembly connector to the system cryoprobe connector to the cryoprobe return line, and into the dewar. In some embodiments, rather than returning to the dewar, cryogen may flow as above except that it enters the atmosphere through a vent connected to the return lumen of the cryoprobe or the flexible return lumen of the cryoprobe insulated supply hose.

While system cryoprobe connectors are typically mounted to the device, some embodiments provide a permanent hose system that extends from the device and a connector at the distal end of the hose system. The permanent hose system may extend the length of the cryogen supply line, and if provided, the cryogen return line.

Cryoprobe Return Line

In some embodiments, the system comprises a cryoprobe return line extending from the system cryoprobe connector to the dewar. The cryoprobe return line functions to return cryogen from the cryoprobe to the dewar. As noted above, in open an system, cryogen vents to the atmosphere downstream from the cryoprobe freeze zone. In some embodiments, the cryogen is recaptured for further use. In such embodiments, the cryogen passes through the flexible return lumen of the insulated supply hose, into the system cryoprobe connector and into the cryoprobe return line which delivers the cryogen back to the dewar.

Multiple Cryoengines

In some embodiments, a second cryoengine is provided in which sub-cooled supercritical nitrogen is generated while the first cryoengine is being used to supply sub-cooled supercritical nitrogen to the one or more cryoprobes. As the first cryoengine empties and the pressure of the sub-cooled nitrogen from the first cryoengine decreases, if the cryogenic procedure is required to continue, the supply of sub-cooled supercritical nitrogen to the distribution assembly can be switched or toggled from the first cryoengine to the second cryoengine by way of a valve connected to the first and second cryoengines and the cryogen distribution assembly such that continuous flow of sub-cooled supercritical nitrogen to the cryoprobes is maintained. After toggling to the second cryoengine, the first cryoengine can be refilled, charged (or pressurized) in the same manner it was originally prepared and used to provide sub-cooled supercritical nitrogen when the second cryoengine empties. If two or more cryoengines are used, each cryoengine will have similar components and be of similar construction to that described in detail with respect to the first cryoengine.

Methods

In the methods disclosed herein, supercritical nitrogen is generated from a combination of liquid nitrogen and nitrogen gas at the specific volume ratios disclosed herein. Supercritical nitrogen is generated when the pressure is increased to greater than critical pressure (493 psi) and the temperature is greater that critical temperature of nitrogen (−147° C.). The supercritical nitrogen that is generated in the cryoengine is sub-cooled; it retains properties of supercritical nitrogen while being at a temperature lower than the critical temperature. According to the methods disclosed herein, flow of sub-cooled supercritical nitrogen through the cryoprobe can be initiated and the nitrogen can pass through a cryoprobe's small diameter cryoprobe supply lumen and cryoprobe return lumen without its flow being prevented or impeded by the fluid properties of a liquid, particularly, a cold liquid such as liquid nitrogen. As sub-cooled, supercritical nitrogen, the nitrogen can flow through structures the size of the cryoprobe supply lumen and into the freeze zone and through to the return lumen without the physical challenges and limitations that exist when attempts are made to circulate a liquid or other fluid with relatively high viscosity as compared to supercritical nitrogen (which is capable of frictionless flow), through structures the size of the cryoprobe supply lumen and into the freeze zone and through to the return lumen. As a sub-cooled fluid, the sub-cooled supercritical nitrogen can absorb heat without transitioning to nitrogen gas and causing vapor lock in the lines in the system through which the sub-cooled supercritical nitrogen flows. As sub-cooled supercritical nitrogen flows through the freeze zone, heat is removed from the objects in contact with the cryoprobe shaft adjacent to the freeze zone. The removal of heat from cells and tissue causes the cells and tissue to freeze and as a result, die.

The methods use sub-cooled supercritical nitrogen that is circulated through the cryoprobe including through the supply lumen 4 of the cryoprobe, into the freeze zone 8 and into and through the return lumen 6. The sub-cooled supercritical nitrogen remains colder that the critical temperature of nitrogen (−147° C.) as it flows through the system, the temperature of the sub-cooled supercritical nitrogen is below the critical temperature of nitrogen (−147° C.) as it exits the cryoengine and returns from freeze zone of the cryoprobe below the critical temperature of nitrogen, i.e. its temperature never reaches the temperature above which it transitions to gas. The sub-cooled supercritical nitrogen does not vaporize or transition to a gas when contacted with live tissue and absorbing heat in amounts sufficient to form ice balls. The absence of vaporization or transitioning to a gas avoids the occurrence of vapor lock resulting in continuous, unimpeded flow.

The initial operating pressure of the sub-cooled supercritical nitrogen is 1000 psi or greater, typically 1200-1300 psi or greater. As the system operates, the operating pressuring steadily decreases from the initial high pressures provided to charge the system and commence nitrogen flow to the cryoprobe. Eventually, the pressure decreases below critical pressure to 300 psi or less. Nevertheless, the sub-cooled nitrogen continues to flow unabated, allowing for continued cooling of the surface of the cryoprobe for an extended period of time.

In some embodiments, liquid nitrogen is added to the cryoengine at a temperature of about −196° C. and at ambient pressure. One or more internal heat sources in the first tank are activated and the nitrogen pressure is raised to at least 1000 psi or more, which is above nitrogen's critical pressure of 493 psi. Starting at pressures of about 1000-1300 psi, for example 1250 psi, supercritical nitrogen can be delivered to the cryoprobe freeze zone for at least about 45 seconds to 1 minute. The temperature of the sub-cooled supercritical nitrogen delivered to the cryoprobe is between about −165° C. and −170° C., such as −168° C. As the nitrogen leaves the cryoengine for delivery to the cryoprobe, the pressure drops steadily over an extended period of time until it reaches about 80 psi, at which point the temperature is about −160° C. to about −170° C. If procedures are continued thereafter and the system comprises a second cryoengine, the system switches or toggles over to the second cryoengine in which sub-cooled supercritical nitrogen has been generated and is waiting for delivery to the cryoprobes. Therefore, for extended cryotherapy procedures, sub-cooled supercritical nitrogen can continuously be delivered to the cryoprobes without interruption. After use of the second cryoengine commences, first cryoengine can begin a new cycle of charging.

Provided herein are cryoablation methods, cryosurgical methods and other methods that include cooling a surface of a cryoprobe, as well as cryogenic systems useful in performing such methods. The cryogen used is nitrogen. Sub-cooled supercritical nitrogen circulated through a cryoprobe is used to cool an external surface of the cryoprobe and freeze tissue in contact with the external surface. The cryoprobe external surface that is cooled is the external surface of the cryoprobe's freeze zone. The internal structure at the freeze zone is typically a chamber or compartment within a cryoprobe where the cryoprobe's supply lumen transitions to the cryoprobe's return lumen. The external surface of the cryoprobes freeze zone is in thermal communication with the internal volume of the freeze zone such that heat can be efficiently conducted from the external surface to sub-cooled supercritical nitrogen in the freeze zone. Locations in the cryoprobe other than the freeze zone are typically insulated or otherwise have controlled temperatures so that these other external surfaces are not efficiently cooled by the circulating sub-cooled cryogen. Thus the freezing effect is localized to a specific external surface of the cryoprobe.

In the methods and systems disclosed herein, the temperature of the nitrogen that is supplied and delivered to the cryoprobe freeze zone is at its sub-cooled temperature prior to entering the freeze zone. That is, unlike other systems that rely on generating cold temperatures by volume expansion of pressurized gas (the Joule-Thomson effect), or by endothermic phase transition such as evaporation that produces cold temperatures, methods and systems disclosed herein rely upon circulating sub-cooled nitrogen.

As the sub-cooled supercritical nitrogen flows through the cryoprobe freeze zone, heat is conducted from the external surface of the cryoprobe to the circulating sub-cooled nitrogen, cooling the external surface to temperatures levels sufficient to freeze tissue in contact with the external surface of the cryoprobe, thereby forming lethal ice.

Embodiments of the present systems may comprise one or more cryoengines that can generate sub-cooled, supercritical nitrogen which is used in the methods. The terms "cryogenic system" and "system" are used interchangeably and refer to the device or devices that generate sub-cooled, supercritical nitrogen and provide it for distribution. While various arrangements may be provided, the cryogenic systems generally comprise one or more cryoengines, a dewar, a cryogen distribution assembly connected to the one or two or more cryoengines, there being a valve between the cryogen distribution assembly and the one or two or more cryoengines, one or more system supply lines, and one or more cryoprobe connectors. In some embodiments, the system further comprises one or more system return lines. The system comprises at least one cryoengine that heats, pressurizes and sub-cools.

Some methods use systems that comprise a single cryoengine while other use systems that comprise two or more cryoengines. Systems that have multiple cryoengines have the advantage of being able to be used for extended periods of time because one or more cryoengines may be actively generating sub-cooled supercritical nitrogen while sub-cooled supercritical nitrogen is being dispensed and circulated to cryoprobes. In single cryoengine systems, methods must be discontinued when a cryoengine dispensing nearly all of its sub-cooled supercritical nitrogen or the pressure drops to a low level. Discontinuation and delay caused by the time consuming re-filling of the cryoengine and generation of sub-cooled supercritical nitrogen can be avoided when multiple cryoengines are provided.

In systems comprising multiple cryoengines, the cryoengines may be connected to a single distribution assembly and valves can be provided so that one cryoengine can be supplying sub-cooled supercritical nitrogen to the distribution assembly and on to the cryoprobes while simultaneous, sub-cooled supercritical nitrogen is being generated in a second cryoengine that is closed off from the distribution assembly. Flow of sub-cooled supercritical nitrogen from one cryoengine may be initiated as flow from another cryoengine is discontinued. Switching can be initiation when the cryoengine that is dispensing sub-cooled supercritical nitrogen is nearly depleted. The system is designed for the pressure in the cryoengine to decrease as sub-cooled supercritical nitrogen is distributed from the cryoengine to the cryoprobes. As the cryoengine becomes nearly empty, the pressure may drop to or below critical pressure of nitrogen. In such cases, the nitrogen remains pressurized and is sub-cooled. The system is designed so when the pressure falls below critical pressure, the nitrogen is at a temperature and pressure where it is pressurized liquid nitrogen, not nitrogen gas. That is, once the nitrogen in the system is supercritical nitrogen and the system is ready to flow sub-cooled supercritical nitrogen to the cryoprobes, the nitrogen exists as sub-cooled supercritical nitrogen or, as the pressure decreases, pressurized liquid nitrogen. In embodiments comprising multiple cryoengines which can be using in processes involving uninterrupted flow, the nitrogen is initially delivered to cryoprobes as sub-cooled supercritical nitrogen. When the pressure decreases to sub-critical pressure, pressurized liquid nitrogen is circulated until the system closes the valve from the first cryoengine that is at sub-critical pressure and the valve from the second cryoengine is opened and sub-cooled supercritical nitrogen is delivered to the cryoprobes. The process can continue by re-filling the first cryoengine and generating sub-cooled supercritical nitrogen while the second cryoengine is used to supply sub-cooled supercritical nitrogen to the cryoprobes. When the second cryoengine becomes depleted, the valves from the second cryoengine may be closed and the valve for the first cryoengine opened so that the first cryoengine again supplies sub-cooled supercritical nitrogen to the cryoprobes. This process of alternating between cryoengines can continue until the procedures is completed or the liquid nitrogen bath reaches its minimum operating level. The switching from one cryoengine as the source of sub-cooled supercritical nitrogen to a different cryoengine as source of sub-cooled supercritical nitrogen may be referred to as toggling and may be performed multiple times to deliver sub-cooled supercritical nitrogen to cryoprobes for an extended period of time.

The sub-cooled supercritical nitrogen is generated using a combination of liquid nitrogen and gaseous nitrogen maintained in fluid communication with each other in a cryoengine that includes a closed tank system having one or more tanks. The starting volumes of liquid nitrogen and nitrogen gas are provided within a range of ratios. In some embodiments, the volume ratio of liquid nitrogen:nitrogen gas is in a range selected from the group of ranges consisting of: from about 0.80:1.00 to about 1.00:0.80, from about 0.85:1.00 to about 1.00:0.85, from about 0.90:1.00 to about 1.00:0.90, and from about 0.95:1.00 to about 1.00:0.95. In some embodiments, the volume ratio of liquid nitrogen: nitrogen gas is about 1.00:1.00.

"Closed tank system" refers to a cryoengine with a single tank or a cryoengine with two or more tanks in which the tank interiors are in fluid communication with each other. In cryoengines having two or more tanks, the tanks may be connected by tank conduits and tank valves provided that the tank valve can be configured so that the tank interiors are in fluid communication with each other while the tanks are sealed from the outside. Having an interior that is sealed from the outside refers to the capability of the tanks to be pressurized. Typical cryoengines having two tanks connected by a tank conduit and tank valve are disclosed above. As noted above, in some embodiments, the ratio of the volume of the first tank volume to volume of the second tank may be a ratio of about from 0.75:1 to 1:0.75, with variations disclosed above a ratio of the volume of the first tank volume to volume of the second tank of about 1:1.

Initial, when the liquid nitrogen bath is full, the cryoengine being partially submersed in a liquid nitrogen bath. Typically, between about 40% to about 50% of the external surface area of the cryoengine is in contact with liquid nitrogen. These submersed portions of the cryoengine being function as a heat exchanger. In systems that include two tank cryoengine designs, when the liquid nitrogen bath is full, one tank is usually fully or partially submerged in liquid nitrogen and the other tank is not in contact with liquid nitrogen and is usually outside of the dewar. If partially submersed, the first tank is submersed 80% or more, in some embodiments 85% or more, in some embodiments 90% or more, and in some embodiments 95% or more when the liquid nitrogen bath is full. As liquid nitrogen is depleted, less or the first tank is submerged. Eventually, most of the liquid nitrogen bath may be dispersed but preferably at least 5-10% of the first tank remains submerged together with the distribution manifold and the portions of the cryoprobe system supply lines.

Liquid nitrogen is added to the dewar from an external liquid nitrogen source, typically through an opening in the dewar provided for such a function. The liquid nitrogen is added to an amount between a level at the fill level and the re-fill level, usually to the fill level. After filling, the external liquid nitrogen source may be disengaged from the device. Upon filling the dewar to produce the liquid nitrogen bath, the submerged or partially submerged first tank can act as a heat exchanger between the liquid nitrogen bath and the contents (nitrogen) of the first tank.

In addition to functioning as a heat extracting medium for the heat exchange function of the first tank, the liquid nitrogen bath also provides a source of liquid nitrogen that can be used to fill the cryoengine's first tank. In some embodiments, the first tank may be filled with liquid nitrogen from an external source. The portability of the system being a practical feature, the use of the liquid nitrogen bath as the reservoir from which the first tank is filled allows for filling the first tank as a self-contained unit without the need to attach the system to an external nitrogen source. In some embodiments, the first tank is filled with liquid nitrogen from the liquid nitrogen bath by activating a submersible pump connected to the first tank inlet port, the submersible pump being submersed in the liquid nitrogen bath. The full or partial submersion of the first tank in the liquid nitrogen bath provides the advantage in operation in that liquid nitrogen can be added to the first tank at a rate which is not overly time consuming. Designs in which a tank to be filled with liquid nitrogen is not fully or partially submerged in liquid nitrogen require significantly longer amounts of time to fill the tank because of the evaporation and transitioning of liquid nitrogen to gaseous nitrogen (boil-off). When the first tank is cooled as is the case when it is submersed in the liquid nitrogen bath, filling proceeds more rapidly because boil-off is minimized. With the exception of the first tank vent valve, during filling, valves connecting the interior of the first tank to other components of the system are closed except the tank conduit valve, if present, may be opened, although it is typically closed during filing. The first tank vent valve is opened to allow nitrogen gas to escape the tank as liquid nitrogen displaces the gaseous nitrogen that forms in the tank as a result of minimal boil-off upon filling the tank. In some embodiments, the first tank has sensors to monitor and indicate the level of which it is filled with liquid nitrogen. In some embodiments, sensors are a series of spaced temperature sensors disposed longitudinally. As the tank becomes filled, the temperature sensors detect the temperature of liquid nitrogen indicating the level of liquid nitrogen in the tank. When the first tank is filled, the first tank vent valve is closed and the submersible pump is deactivated. The valve connecting the submersible pump to the first tank is then closed. Typically, the valve is a check valve that automatically opens to allow liquid nitrogen to be pumped from the dewar into the first tank and automatically closes when the pump is deactivated and/or the back pressure in the first tank exceeds the forward pressure created by the pump.

As noted above, the tank conduit valve, if present, may be opened or closed. In typical embodiments, the tank conduit valve is present and is closed. When the first tank is full and the system is ready for pressurization, i.e., all valves that connect the interior of the tanks to the exterior being closed, the tank conduit valve is opened and the interior of the first and second tanks are placed in fluid communication with each other.

At this point, the cryoengine may be charged, i.e., its contents pressurized with heat. As described above, the first tank comprises an internal heat source. In some embodiments, the internal heat source comprises one or more immersion heaters. Activation of the internal heat source causes an increase in temperature of the nitrogen that is in direct contact with the heat source. As noted above, the first tank, which is at least partially submerged in the liquid nitrogen bath, functions as a heat exchanger. As heat is added to the first tank by the internal heat source, some heat is also drawn out by the heat exchanger activity of the first tank, sub-cooling nitrogen in the first tank. Additional heat may be added in embodiments in which the second tank is in contact with external heating sources. Initially, the pressure in the cryoengine is below the critical pressure of nitrogen. As heat is added by the activated internal heat source, the pressure within the cryoengine (in both the first and second tanks) increases uniformly to levels higher than the critical pressure of nitrogen. External heat sources in direct contact with portions of the non-submersed exterior surface of the tank assembly including non-submersed portions of the first tank and/or the tank conduit and/or the second tank are optionally provided in some embodiments. These external heat sources may be insulated blankets or jacket heaters, drum blanket heaters, heating tape and the like.

As heating continues, the pressure in the cryoengine increases. One or more pressure sensors may be used to monitor the pressure. Pressure sensors may be located in the first tank, the second tank and/or the tank conduit for example. Internal pressures may reach 1000 psi or more. Because the first and second tanks are in fluid communication with each other at this point, the pressure in the closed tank system is uniform. The pressure in the closed tank system increases uniformly to levels above the critical pressure of nitrogen and well beyond as heat continues to be added to the system at a rate greater than it is removed by the liquid nitrogen bath. As noted above, operating pressures ranging from above nitrogen critical pressure to 1000 psi or more, 1050 psi or more, 1100 psi or more, 1150 psi or more, 1200 psi or more, 1250 psi or more, 1300 psi or more, 1350 psi or more, 1400 psi or more, 1450 psi or more, 1500 psi or more, 1550 psi or more, 1600 psi or more, 1650 psi or more, 1700 psi or more, 1750 psi or more, 1800 psi or more, 1850 psi or more, 1900 psi or more, 1950 psi or more, 2000 psi or more may be generated. The temperature is variable within the cryoengine. Heat is added to the interior of the first tank and the exterior of the second tank while it is withdrawn from the first tank by the liquid nitrogen bath. The temperature of the nitrogen in the first tank is variable as it being both heated by direct contact with the high temperature internal heat sources while simultaneously being sub-cooled through its contact with the surface of the first tank, which is in thermal communication with the liquid nitrogen bath. The temperature at the internal heat source is greater than the critical temperature of nitrogen. The temperature of the nitrogen in contact with the internal heat source increases rapidly and then rapidly decreases as it is cooled by the heat exchange activity of the first tank submerged in the liquid nitrogen bath. Heat is removed from the contents of the first tank and transferred to the liquid nitrogen bath. A temperature gradient extends axially from the internal heat source to the portions of the first tank that are made of thermally conductive material and that have external surfaces that are in contact with liquid nitrogen of the liquid nitrogen bath. The temperature rapidly decreases along the gradient as measured from the internal heat source to sites inside the submerged portions of the first tank. Temperature sensor may be provided inside the first tank such as between the internal heat source and the tank wall. Temperature at that location typically indicate that the temperature of the pressurized nitrogen is between about −155° C. and about −165° C., usually about −160° C. to about −170° C. The temperature is higher at the internal heat source and lower at the tank wall. Heat is continuously added by the internal heater source and, if provided, the external heaters. The temperature in the second tank exceeds nitrogen's critical temperature of −147° C., typically being between 40° C. and 80° C.

The system is dynamic. Heat is added by the internal heaters and, if provided, by the external heaters. Simultaneously, heat is removed by the heat exchange action of the first tank that is fully or partially submerged in a liquid nitrogen bath. As the pressure increases above the critical pressure of nitrogen, about 492 psi, supercritical nitrogen is formed from nitrogen with a temperature greater that the critical temperature of nitrogen, about −147° C. When the pressure is raised to a pressure greater than critical pressure, the pressurized nitrogen gas in the second tank and tank conduit under the high pressure conditions, the liquid nitrogen that is heated to a temperature above critical temperature becomes supercritical nitrogen. As the contents of the first tank circulate, liquid nitrogen is converted to supercritical nitrogen and supercritical nitrogen becomes sub-cooled by the heat removal that occurs by thermal conduction from the contents of the first tank to the liquid nitrogen bath. The cryoengine comprises sub-cooled supercritical nitrogen.

The pressure of the nitrogen in the fully charged cryoengine may be greatly in excess of the critical pressure of nitrogen. The temperature of the nitrogen in the cryoengine varies depending upon its localized position in the cryoengine. The nitrogen in direct contact with internal heat source is rapidly heated and cooled by the nitrogen in the first tank which is not in direct contact with the internal heat source. The nitrogen in the first tank is sub-cooled by the heat exchange activity of the first tank submerged in the liquid nitrogen bath. The nitrogen in the second tank may be heated by external heat sources to temperatures in excess of critical temperature. When the supercritical nitrogen reaches a pressure of 500 psi or more, typically about 1000 psi, 1100 psi, 1200 psi, 1300 psi, 1400 psi, 1500 psi, 1600 psi, 1700 psi, 1800 psi, 1900 psi, 2000 psi or more, the system may be used in cryoablation methods, cryosurgical procedures and other methods that include cooling a surface of a cryoprobe. The cryogen flowing through the cryoprobe may be vented into the atmosphere or circulated back into the dewar.

The valve connecting the distribution assembly to the first tank exit port, the first tank exit valve, is opened and sub-cooled supercritical nitrogen flows through the distribution assembly to the one or more cryoprobes connected to the apparatus. In some embodiments, the sub-cooled supercritical nitrogen exits the cryoengine through a port submersed in the liquid nitrogen bath and through the distribution assembly, also be submersed in the liquid nitrogen bath.

Supercritical fluids flow in a manner similar to gas but have heat absorption properties similar to liquids. Flowing through components submersed in the liquid nitrogen bath, further sub-cools the sub-cooled supercritical nitrogen prior to its delivery to the one or more cryoprobes. Flowing in a manner more similar to a gas than a liquid, the sub-cooled nitrogen can pass through the small diameter supply lumen of the cryoprobe to and through its return lumen and continues to flow through the supply lumen of the cryoprobe to and through its return lumen even as its pressure drops. The sub-cooled, supercritical nitrogen can flow through the cryoprobe including the supply lumen of the cryoprobe which has a narrow inner diameter which can impede the flow of some liquids. For each cryoprobe, the sub-cooled supercritical nitrogen flows through the flexible supply lumen of the flexible insulated hose, through the cryoprobe supply lumen, through the freeze zone, through the cryoprobe return lumen, through the flexible return lumen of the flexible insulated hose, and either into a venting component for release into the atmosphere or into the system return line and the dewar.

Similar to the behavior of a liquid, the nitrogen delivered to the freeze zone can efficiently absorb heat from living tissue and form ice balls. The sub-cooled, supercritical nitrogen can absorb heat transferred through the thermally conductive cryoprobe shaft at the freeze zone, cooling the cryoprobe shaft at the freeze zone, which is typically located at the distal tip of the cryoprobe shaft, such that ice forms. Despite its rapid and effective removal of heat from tissue and formation of ice balls, the temperature of the cryogen does not increase such that it reaches the temperature where is evaporates into a gas. As the system continues to run, ice balls form to sizes sufficient to eliminate tissue surrounding cryoprobe. Ice balls having diameters of from about 5 mm or less to about 40 mm or more may be generated, effectively eliminated viable tissue at the site of the ice ball. In some embodiments, ice balls may be generated that have diameters of from about 5 mm or less to about 10 mm or more, from about 5 mm or less to about 15 mm or more, from about 5 mm or less to about 20 mm or more, from about 5 mm or less to about 25 mm or more, from about 5 or less mm to about 30 mm or more, from about 5 mm or less to about 35 mm or more, from about 5 mm or less to about 40 mm, where reference to about 5 mm or less in this sentence refers to 1 mm, 2 mm, 3 mm or 4 mm. In some embodiments, ice balls may be generated that have diameters of from about 5 mm to about 20 mm or more, from about 5 mm to about 25 mm or more, from about 5 mm to about 30 mm or more, from about 5 mm to about 35 mm or more, from about 5 mm to about 40 mm or more, from about 10 mm to about 15 mm or more, from about 10 mm to about 20 mm or more, from about 10 mm to about 25 mm or more, from about 10 mm to about 30 mm or more, from about 10 mm to about 35 mm or more, from about 10 mm to about 40 mm or more, 15 mm to about 20 mm or more, from about 15 mm to about 25 mm or more, from about 15 mm to about 30 mm or more, from about 15 mm to about 35 mm or more, from about 15 mm to about 40 mm or more, from about 20 mm to about 25 mm or more, from about 20 mm to about 30 mm or more, from about 20 mm to about 35 mm or more, from about 20 mm to about 40 mm or more, from about 25 mm to about 30 mm or more, from about 25 mm to about 35 mm or more, from about 25 mm to about 40 mm or more, from about 30 to about 35 mm or more, from about 30 mm to about 40 mm or more, from about 35 mm to about 40 mm or more. While the cryoprobes are very effective in transferring heat from the tissue to the cryogen in the system, the temperature of the cryogen does not increase very much. The sub-cooled, supercritical nitrogen is very effective in absorbing heat. After the sub-cooled, supercritical nitrogen initiates flow through the narrow lumens of the cryoprobe, flow may continue unabated including the flow of pressurized liquid nitrogen. When the pressure decreases below critical pressure, the temperature of the sub-cooled nitrogen remains sufficiently low that the cryogen does not convert to a gas phase. At pressures below critical pressure, the temperature is always sufficiently low to maintain the cryogen as pressurized liquid nitrogen. By using sub-cooled supercritical nitrogen and pressurized liquid nitrogen, low temperature cryogen may be employed with vapor lock occurring.

When the nitrogen in the cryoengine is nearly completely depleted or when the pressure decreases to a predetermined level, such as for instance about 300 psi to 500 psi, the procedure may be discontinued of, if the system comprises a second cryoengine, the procedure may continue using cryogen from the second cryoengine. In some embodiments, the predetermined level for discontinuing the procedure or switching to a second cryoengine as a source of cryogen may a pressure of 500 psi or less, 450 psi or less, 400 psi or less, 350 psi or less, 300 psi or less, 250 psi or less, 200 psi or less, 150 psi or less, or 100 psi or less. As noted above, once the pressure becomes less than the critical pressure of nitrogen, the temperature must be sufficiently low to maintain the cryogen in liquid form as pressurized liquid nitrogen so that vapor lock does not occur.

Thus, the methods achieve cryogen flow through lumens with very small lumens through which liquid nitrogen under ambient conditions cannot pass, and rapid and efficient absorption of heat from live tissue with the formation of nitrogen gas and the vapor lock attendant with such evaporation. Moreover, the system is robust and can be used to perform multiple procedures.

Some embodiments are variation of methods using two tank designs. As can be readily appreciated, some alternative embodiments may provide cryoengines with three or more tanks, the interiors of which are in fluid communication with each other. Some embodiments, provide systems and methods using single tank designs. In such single tank embodiments, the cryoengine provides a single tank. The system is designed for partial submersion of the single tank in the liquid nitrogen bath with a significant portion of the single tank being outside the liquid nitrogen bath so that the upper part of the single tank functions as the second tank. Upon filling, the single tank is filled to a ratio of 0.75:1 to 1:0.75 liquid nitrogen to nitrogen gas. Ratios of liquid nitrogen to nitrogen gas set forth above for two tank system may be applied in the single tank system.

In some embodiments, the cryoprobe is at least partially inserted into the body so that the freeze zone 8 is positioned in contact with tissue and cells to be destroyed. The cooling of the exterior surface of the cryoprobe is useful to eliminate the unwanted tissues by reaching freezing temperatures, which kill the tissue in contact with the cryoprobe and by forming ice balls. The ice balls form from water within the tissue and effectively kills the tissue upon freezing. Typically, during a cryotherapy procedure, multiple freeze/thaw cycles are performed in order ensure the unwanted tissue and cells are completely killed. These cycles may be a 10 minute freeze, followed by a 5 minute thaw, followed by another 10 minute freeze. Cell death typically occurs at −40° C.

Examples of unwanted tissue include: tumors, a gland or organ that comprises cancerous cells such as a prostate gland in a patient diagnosed with prostate cancer, tissue comprising cancer cells such as esophageal cancer, kidney cancer, liver cancer, breast cancer, tissue comprising hyperplasic cells such as Barrett's esophagus and hyperplasic cervix. In addition, some embodiments, the cryobody is at least partially inserted into tissue so that it comes into contact with cardiovascular tissue to treat arrhythmias or unblock blood vessels. Depending upon the application, different cryoprobes may be used such as those with rigid needle like elongated wand-line structures and flexible elongated wand-like structures such as cryocatheters such as for used in vascular and cardiovascular applications.

EXAMPLES

Example 1

In order to achieve an overall supercritical nitrogen ("SCN") cryogen delivery length of greater than 35 feet (from the console to the probe tip) a specialized satellite unit with an integrated umbilical was designed and developed. The satellite unit consists of a 16.5 in×11 in×37 in unit on casters containing an interface plate with four probe connection ports, four thermocouple connections and four probe thaw electric port connections. These ports and connections are integrated with a 25 foot umbilical which contains four individual cryogen supply lines contained within a pre-cooling liquid nitrogen ("$LN_2$") jacket line, one common cryogen return line four thermocouple wires and one low voltage (12 V) DC thaw power line all of which interface with the console to allow for cryoprobe operation. With the design of the total system being such that the satellite unit umbilical connects to the console and the probes connect to the satellite unit, the delivery of SCN cryogen over a distance of greater than 35 feet is accomplished with only two connections within the cryogen delivery path between the cryoengine console and the probe tip. The quad supply line design within the umbilical allowed for the placement of the cryogen flow control solenoids on the console, remote from the satellite unit while still allowing for independent operation of all four cryoprobes.

Part of the design objective of the SCN MRI System was to develop a design That would allow for its utilization within an MRI setting. In order to accomplish this objective, the system was divided into two sub system assemblies where in the main console, housing the electronics, computer, valving, dewar, cryoengine, was designed to remain outside the MRI suite whereas the satellite unit housing the probe connection bulkheads could be placed within the suite. The main console and the satellite unit were connected by a single umbilical. Up to four cryoprobes were then attached to the satellite unit to allow for freezing. Overall the design of the SCN MRI Prototype System and prototype cryoprobes accomplished the successful delivery of SCN to the cryoprobe tip (all prototype probe configurations including 1.5 mm, 1.8 mm, 2.0 mm 3.4 mm, 6 mm and 7 mm diameter tips) over a total distance of ~38 feet with only two points of connection. Further, the performance of the prototype SCN MRI System was found to be comparable to that of the previously delivered prototype 8 Port SCN Systems.

All raw materials utilized with in the umbilical and satellite unit consisted of non-ferromagnetic materials. These materials include various plastics, 316 stainless steel, manganin and copper wire, aluminum or brass all of which are established as nonmagnetic and listed as MRI compatible. Specifically, the components of the satellite unit and umbilical consisted of aluminum rails and stainless steel hardware for the satellite frame, 316 stainless steel ("SS") tubing and Swagelok parts, PTFE plastic supply jacket and return lines, aluminum bulkhead mounting plate, ABS plastic satellite unit skins and base plate, plastic casters with solid 316 stainless steel axle, plastic encased thermocouple bulkhead connectors, etc. As with all the previous prototype cryoprobes, all cryoprobes developed under MS6 consisted of a ULTEM plastic connector, sylcron plastic outer sheath, polyamide plastic return tube, 316SS supply tube, and a combination 315SS/Brass cryoprobe needle assembly. The one alteration in the material of the new cryoprobes was the replacement of the 36 gauge Nicrome 60 resistance wire heater with a 40 gauge manganin resistance wire in the 1.5 mm×3 cm needle cryoprobes. The reduction in size and material change was necessary due to the reduced landscape within the lumen of the 1.5 mm cryoprobe allowing for the fitting of the heater coil within the 1.5 mm cryoprobe while keeping the resistance (~20 ohms) and power (~7 watts) the same across all probe sizes.

The umbilical was unique in its design wherein four independent SCN supply lines (18XT 316SS tubing) running from the console to the satellite bulkheads probe connectors (one per probe connection bulkhead) were contained within a ⅜ in diameter PTFE (plastic) tube (referred to as the Supply Jacket). The supply lines and Supply Jacket were further encased within another ½ in diameter PTFE tube which served as a common cryogen return line for all four probes. This ½ in. inner diameter common return tube was then wrapped in a Mylar insulation jacket, placed into a foam insulation tube and then the four thermocouple wire and DC heater wire connection leads were attached to the exterior of the insulative foam tube. This assembly was then enclosed in a nylon mesh shell for the finished outer surface of the umbilical. At the main console end of the umbilical, the four supply lines, supply jacket and return tube were diverged from their coaxial configuration allowing for each line, 6 in total (four supply, one supply jacket, and one return line) to be connected directly to the main console. On the satellite unit end, the umbilical was permanently attached via 316 SS Swagelok connections to connect the supply and return lines from the umbilical to the four independent probe connection bulkheads contained in the satellite unit to which cryoprobes can be attached for use. Through this configuration, the satellite unit and main console are easily attached for use and detached for storage. When detached for storage, the satellite unit base contains a cabinet for which the umbilical can be stored in. When the main console and satellite unit are attached via the umbilical for use, Cryoprobes are attached to the satellite unit via the standard prototype bulkhead connection for use.

The utilization of four independent supply lines allowed for the individual control of each of the probe ports while eliminating the need for control solenoid valves to be placed within the satellite unit. Instead the supply solenoid valves were able to be placed on the main console located outside of the MRI suite. The Supply Jacket containing the four supply lines was incorporated into the umbilical design to allow for precooling of the supply lines exterior with LN2 thereby eliminating any parasitic heat gain along the length of the umbilical during system operation. This was necessary as parasitic heat gain from the environment can cause warming and boiling of SCN thereby creating choking flow and preventing proper freezing of the probes. The Supply Jacket connection was intergraded into the face connection face place of the main console and was plumed to the dewar LN2 fill line via a T-connection in the fill line prior to entry into the dewar. To control the flow of LN2 to either the dewar (for fill), Supply Jacket (for umbilical cooling) or both (simultaneous dewar fill during system running) a solenoid valve was inserted into both the fill and cryogen jacket lines after the T-connection split of the lines. These solenoid were wired into the user interface thereby allowing the user to independently control the opening and closing of either valve at will. The common return line was utilized to allow for a larger return lumen volume thereby accommodating the return volume of SCN from the probes, LN2 from the supply jacket, and cold N2 gas which formed as a result of heat gain during the return of the cryogen over the length of the umbilical. Further this design helped to reduce/eliminate the potential for the creation of any increased pressure (back pressure) on the return line which could affect overall cryogen flow and system performance.

Example 2

An apparatus for generating sub-cooled pressurized nitrogen is provided. The sub-cooled pressurized nitrogen can be used in combination with one or more cryoprobes methods for cooling an exterior surface of a cryoprobe shaft. In some methods, the one or more cryoprobes that may be used comprise a cryoprobe shaft, a cryoprobe supply lumen, a cryoprobe return lumen, and a freeze zone in fluid communication with the cryoprobe supply lumen and the cryoprobe return lumen, the freeze zone having an interior surface in thermal communication with an external surface of the shaft. The apparatus comprises a dewar, a cryoengine, a supply line and a valve connecting the cryoengine to the supply line.

The dewar is adapted to contain a liquid nitrogen bath. The dewar may further comprise a dewar lid The cryoengine is at least partially disposed within a dewar and positioned for about 40% to about 50% of the cryoengine to be submerged within a liquid nitrogen bath in the dewar. The cryoengine is also adapted to generate sub-cooled, pressurized nitrogen at a pressure of 1000 psi or greater and a temperature of about −160° C. or about −170° C. or colder using one or more heat sources, such as at least one internal heat source, to pressurize the nitrogen and using heat exchange between the cryoengine and liquid nitrogen bath sub-cool the heat pressurized nitrogen in the cryoengine.

The supply line is provided to connect the cryoengine to the one or more cryoprobes so that sub-cooled, pressurized nitrogen can flow from the cryoengine to the freeze zone of the cryoprobe. The valve connects the cryoengine to the supply line. The valve is closed during pressurization of nitrogen and opened for continuous flow of nitrogen from the cryoengine to the freeze zone.

The apparatus is adapted for use in a system that comprises the apparatus and a cryoprobe to provide continuous flow of nitrogen from the cryoengine to a freeze zone of a cryoprobe. The system provides nitrogen from the cryoengine to the freeze zone of the cryoprobe by continuous flow of nitrogen at decreasing pressure starting at the initial pressure of 1000 psi or greater, such as 1250 psi or greater, and temperature of about −160° C. to −170° C. or colder. The continuous flow of nitrogen may be provided until pressure of the nitrogen flowing from the cryoengine to the freeze zone reaches 300 psi or less. The temperature of the nitrogen at the freezing zone is generally no warmer than about −158° C. throughout the continuous flow of from the initial pressure of the of 1000 psi or greater to the final pressure of 300 psi or less. The sub-cooled pressurized nitrogen may be sub-cooled supercritical nitrogen. When the pressure drops below the critical temperature of nitrogen, the temperature is sufficiently cold that the nitrogen is pressurized liquid nitrogen and will not vaporize during the performance of the methods.

Example 3

A cryotherapy system is provided that comprises a single tank cryoengine. The system comprises a dewar and optionally a dewar lid, a charge tank, one or more immersion heaters, a submersible pump, a pump-charge tank valve and a distribution assembly. The dewar comprises a liquid tight dewar container and liquid nitrogen in the dewar container. The charge tank comprises a charge tank inlet port, a charge tank bleed valve which is also referred to as a vent valve, a charge tank-conduit connector port, and a charge tank exit port which is also referred to as a first tank or charge tank outlet port. The charge tank inlet port is at or near the bottom of the charge tank. Likewise, the charge tank exit port is at or near the bottom of the charge tank. The vent valve is at or near the top of the tank The charge tank also includes one or more immersion heaters, preferably two immersion heaters. The submersible pump comprises a pump inlet and a pump discharge outlet. The submersible pump is submersed in liquid nitrogen within the dewar container. A pump-charge tank valve is provided between the submersible pump and the charge tank inlet port. The distribution assembly comprises a distribution inlet port, and one or more cryoprobe supply ports. The submersible pump is connected through the pump-charge tank valve to the charge tank by connection of the charge tank inlet port to the pump discharge outlet with the pump-charge tank valve there between. The charge tank is connected to the distribution assembly by connection of the charge tank exit port to the distribution inlet port. A charge tank exit valve is between the charge tank exit port and the distribution inlet port. When the charge tank is filled or pressurized the charge tank exit valve is closed. The charge tank is positioned so that initially, 40% and 60% of the charge tank is submersed in the liquid nitrogen in the dewar and the charge tank filled with liquid nitrogen at a range of 43%-57% of full volume.

The charge tank is filled with liquid nitrogen by activating the submersible pump. Liquid nitrogen from the dewar is pumped into the charge tank. The vent valve is opened to allow air and nitrogen gas to escape as it is displaced by the liquid nitrogen. When filled to about 43%-57% of full volume the submersible pump is deactivated, the vent valve is closed and the immersion heaters are activated and the pressure in the charge tank increases up to 1000-2000 psi. The heat of the immersion heaters raises the pressure and the temperature in the charge tank generating supercritical nitrogen and the charge tank becomes filled with supercritical nitrogen. Because the charge tank is submersed in the liquid nitrogen bath in the dewar, it acts as a heat exchanger, allowing heat to transfer from the charge tank into the liquid nitrogen bath in the dewar. The temperature of the supercritical nitrogen decreases (gets colder) to produce sub-cooled supercritical nitrogen.

Cryoprobes may be attached to the distribution assembly cryoprobe supply ports. Typically one to eight cryoprobes are attached. The charge tank exit valve is opened and cryogen flow to the cryoprobes. Upon initiating flow, the pressure decreases until pressure of the nitrogen flowing from the cryoengine to the freeze zone reaches 300 psi or less.

In some embodiments, the charge tank may have a volume of 0.5 liters or less to 5 liters or more. The charge tank having a volume of 0.5 liters, 1 liter, 1.5 liters, 2 liters, 2.5 liters, 3 liters, 3.5 liters, 4 liters, 4.5 liters, or 5 liters or more.

In some embodiments, there may be one immersion heater within the charge tank, two immersion heaters within the charge tank, three immersion heaters within the charge tank, or four immersion heaters within the charge tank. Immersion heaters may be 500 Watts, 1000 Watts, immersion heater, 1500 Watts, or 2000 Watt.

In some embodiments, the charge tank comprises one or more temperature sensors inside the charge tank.

In some embodiments, the charge tank contains connections to connect the one or more temperature sensors within the charge tank to temperature monitoring equipment outside the charge tank.

In some embodiments, the charge tank comprises multiple temperature sensors inside the charge tank arranged to be at different depths within the charge tank in order to measure temperature at the various depths and allow for nitrogen fill level to be determined.

In some embodiments, the one or more temperature sensors within the charge tank are attached at location near the top within the charge tank.

In some embodiments, the one or more temperature sensors inside the charge tank are thermocouples and the charge tank contains connections to connect the one or more thermocouples within the charge tank to a power source and temperature monitoring equipment outside the charge tank.

In some embodiments, the charge tank comprises one or more pressure sensors inside the charge tank.

In some embodiments, the charge tank contains connections to connect the one or more pressure sensors within the charge tank to pressure gauges or pressure monitoring equipment outside the charge tank.

In some embodiments, the one or more pressure sensors within the charge tank are attached at location near the top within the charge tank.

The pump-charge tank valve is a check valve or an actuated valve such as an electric actuated valve, a pneumatic actuated valve, a hydraulic actuated valve.

The distribution assembly comprises a distribution manifold located at or near the bottom near the top of the charge tank.

The distribution assembly has a single cryoprobe supply port or multiple cryoprobe supply ports such as 2, 3, 4, 5, 6, 7, 8 or more cryoprobe supply ports.

What is claimed is:

1. A cryogenic system for cooling an exterior surface of a cryoprobe comprising:
    a dewar containing a liquid nitrogen bath; and
    at least one cryoengine comprising:
        a first tank positioned at least partially in the dewar and comprising one or more heating elements;
        a second tank disposed outside of the dewar, the second tank comprising an exterior surface that is insulated; and
        a tank conduit fluidly connecting the first tank to the second tank;
        wherein at least a portion of the exterior surface of the second tank is in direct contact with a heat source.

2. The cryogenic system of claim 1, wherein the heat source is an external heater.

3. The cryogenic system of claim 1, wherein the external heater comprises at least one of a blanket heater, a jacket heater, and heating tape.

4. The cryogenic system of claim 1, wherein the dewar comprises a fill level and re-fill level, and 80% or more of the first tank is submerged in the liquid nitrogen bath when an amount of liquid nitrogen in the liquid nitrogen bath is at the fill level and at least 5% to 10% of the first tank is submerged in the liquid nitrogen bath when the amount of liquid nitrogen in the liquid nitrogen bath is at the re-fill level.

5. The cryogenic system of claim 4, further comprising a distribution manifold configured to distribute sub-cooled, pressurized nitrogen, wherein the distribution manifold is positioned in the dewar below the re-fill level.

6. The cryogenic system of claim 4, further comprising one or more system supply lines configured to supply sub-cooled, pressurized nitrogen to one or more cryoprobes, wherein at least a portion of the one or more system supply lines are positioned in the dewar below the re-fill level.

7. The cryogenic system of claim 1, wherein the at least one cryoengine is configured to generate sub-cooled, pressurized nitrogen at a pressure of 1000 psi or greater and a temperature of about −160° C. or colder.

8. The cryogenic system of claim 1, wherein a volume of the first tank is approximately equal to a volume of the second tank.

9. The cryogenic system of claim 1, wherein the at least one cryoengine further comprises a tank conduit valve in line with the tank conduit.

10. The cryogenic system of claim 1, wherein the dewar comprises a fill level to identify a first predetermined level of liquid nitrogen in the dewar representing a full liquid nitrogen bath and a re-fill level to identify a second predetermined level of liquid nitrogen in the dewar representing a minimum amount of liquid nitrogen for the liquid nitrogen bath.

11. The cryogenic system of claim 10, wherein the dewar comprises a fill level sensor configured to determine when an amount of liquid nitrogen in the liquid nitrogen bath is at the fill level and at the re-fill level.

12. The cryogenic system of claim 1, further comprising a submersible pump connected to a cryogen inlet port of the cryoengine and wherein the submersible pump is adapted to pump liquid nitrogen from the liquid nitrogen bath in the dewar into the at least one cryoengine.

13. The cryogenic system of claim 12, further comprising a check valve connected between the submersible pump and the cryogen inlet port that automatically opens to allow liquid nitrogen to move from the dewar when the submersible pump is activated.

14. The cryogenic system of claim 1, further comprising a supply valve connecting the at least one cryoengine to a supply line, the supply valve configured to close during pressurization of nitrogen and open for continuous flow of nitrogen from the at least one cryoengine to a cryoprobe.

15. The cryogenic system of claim 1, wherein the at least one cryoengine is a first cryoengine and the cryogenic system further comprises a second cryoengine arranged in parallel to the first cryoengine.

16. The cryogenic system of claim 15, further comprising one or more valves configured to selectively connect the first cryoengine or the second cryoengine to a distribution assembly.

17. The cryogenic system of claim 15, wherein the second cryoengine comprises a third tank positioned at least partially in the dewar and comprising one or more heating elements, and a fourth tank disposed outside of the dewar.

18. The cryogenic system of claim 17 wherein the fourth tank is in direct contact with a heat source.

19. The cryogenic system of claim 1, further comprising a distribution manifold for coupling the at least one cryoengine to one or more cryoprobes, the distribution manifold positioned at a bottom of the first tank.

* * * * *